United States Patent [19]

Palfreyman et al.

[11] Patent Number: 5,104,883

[45] Date of Patent: Apr. 14, 1992

[54] THIOFORMAMIDE DERIVATIVES

[75] Inventors: Malcolm N. Palfreyman, Upminster; Nigel Vicker, Romford; Roger J. A. Walsh, Rayleigh, all of England

[73] Assignee: May & Baker Limited, England

[21] Appl. No.: 461,547

[22] Filed: Jan. 5, 1990

[30] Foreign Application Priority Data

Jan. 6, 1989 [GB] United Kingdom ............... 8900245
Jan. 6, 1989 [GB] United Kingdom ............... 8900295

[51] Int. Cl.$^5$ .................. A61K 31/44; A61K 31/47; C07D 217/06; C07D 401/04
[52] U.S. Cl. .................. 514/311; 514/307; 514/318; 514/340; 514/343; 514/346; 514/357; 514/247; 514/269; 514/255; 514/415; 514/365; 546/146; 546/147; 546/174; 546/175; 546/281; 546/291; 546/330; 546/331; 544/224; 544/335; 544/336; 548/204; 548/469
[58] Field of Search ........... 514/346, 357, 340, 343, 514/318, 311, 307; 546/291, 330, 331, 194, 275, 281, 146, 147, 175, 174.

[56] References Cited

PUBLICATIONS

Chem. Abstracts; vol. 112, No. 1; 7390s (1990).

*Primary Examiner*—Johann Richter
*Attorney, Agent, or Firm*—Morgan & Finnegan

[57] ABSTRACT

Thioformamide derivatives of the formula:

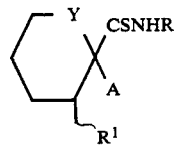

(I)

wherein:
R represents alkyl; A represents an optionally substituted phenyl or heteroaromatic group; $R^1$ represents hydrogen, alkyl, cyano, carboxyl, formyl, carbamoyl, alkoxycarbonyl or a group $-(CH_2)_nOR^2$, $-(CH^2)_nSR^2$, $-(CH_2)_nN(R^2)_2$, $-CH=CHR^3$, $-CH=NOR^4$, $-CONHR^5$, or $-COR^6$; $R^2$ represents hydrogen, alkyl, alkanoyl, aryl, aryl $(CH_2)_n-$ or arylCO—, or, when attached to nitrogen, two $R^2$ groups may together represent alkylene; $R^3$ represents hydrogen; alkyl, alkanoyl, carboxyl, carbamoyl, cyano, aryl, arylCO—, aryl$(CH_2)_n-$, or aryl $(CH_2)_nCO-$; $R^4$ represents hydrogen, alkyl, aryl, aryl $(CH_2)_n-$, optionally substituted alkyl, alkenyl, amino or carbamoyl N,N-disubstituted by alkylene; $R^5$ represents alkyl, aryl, or aryl $(CH_2)_n-$ or an amino acid residue; $R^6$ represents alkyl, aryl, or aryl $(CH_2)_n-$; represents a single or double bond provided that when $R^1$ is formyl represents a double bond; Y represents ethylene, methylene or a direct bond; and n is 1 to 6; and salts thereof possess useful pharmacological properties.

9 Claims, No Drawings

THIOFORMAMIDE DERIVATIVES

This invention relates to new therapeutically useful thioformamide derivatives, to processes for their preparation and to pharmaceutical compositions containing them.

The new thioformamide derivatives of the present invention are those compounds of formula (I), hereinafter depicted wherein:

R represents an alkyl group;

A represents:
  (1) a phenyl group which is optionally substituted, preferably at the 3 and/or 5 position(s), by a halogen atom or a cyano, nitro, trifluoromethyl, carbamoyl, carboxyl, alkoxycarbonyl or alkylsulphonyl group and which may be further substituted by halogen atom(s), alkyl group(s), aryl-containing group(s) having six to twelve carbon atoms, or substituents which form a fused ring thereon; or
  (2) a heteroaromatic group containing 1 or 2 nitrogen atoms selected from pyrid-3-yl, quinolin-3-yl, isoquinolin-4-yl, pyridazin-4-yl, pyrimidin-5-yl, pyrazin-3-yl, indol-3-yl and thiazol-5-yl, optionally substituted by an alkyl or alkoxy group, or a halogen atom;

$R^1$ represents:
  hydrogen; an alkyl, cyano, carboxyl, formyl, carbamoyl, or alkoxycarbonyl group; or a group of the formula $-(CH_2)_nOR^2$, $-(CH_2)_nSR^2$, $-(CH_2)_nN(R^2)_2$, $-CH=CHR^3$, $-CH=NOR^4$, $-CONHR^5$, or $-COR^6$;

$R^2$, each of which may be the same or different when attached to nitrogen, represents:
  hydrogen; an alkyl, alkanoyl, aryl, aryl$(CH_2)_n-$ or arylCO— group; or, when attached to nitrogen, the two $R^2$ groups may together represent an alkylene group having three to six carbon atoms;

$R^3$ represents:
  hydrogen; an alkyl, alkanoyl, carboxyl, carbamoyl, cyano, aryl, arylCO—, aryl$(CH_2)_n-$, or aryl$(CH_2)_n$CO— group; or an alkyl group substituted by a hydroxy, alkoxy, or carboxyl group;

$R^4$ represents:
  hydrogen; an alkyl, aryl, or aryl(CH)$_n-$ group; or an alkyl group substituted by one or more groups selected from carboxyl, alkoxycarbonyl, hydroxy, alkoxy, carbamoyl, N-alkylcarbamoyl, N,N-dialkylcarbamoyl, amino, alkylamino, dialkylamino groups, alkenyl groups having two to four carbon atoms, and amino and carbamoyl groups N,N-disubstituted by an alkylene group having three to six carbon atoms;

$R^5$ represents:
  an alkyl, aryl, or aryl(CH)$_n-$ group; or an amino acid residue wherein the nitrogen atom of the —CONHR$^5$ group is derived from an amine nitrogen atom of the amino acid;

$R^6$ represents:
an alkyl, aryl, or aryl$(CH_2)_n-$ group; aryl indicates: a carbocyclic or heterocyclic, monocyclic or polycyclic, aromatic ring system, preferably phenyl, which may be substituted by one or more substituents selected from halogen atoms and hydroxy, alkyl, alkoxy, cyano, nitro, trifluoromethyl, carboxyl, alkoxycarbonyl, amino, alkylamino, dialkylamino, carbamoyl, N-alkylcarbamoyl, N,N-dialkylcarbamoyl and carboxyalkyl groups, and amino and carbamoyl groups N,N-disubstituted by an alkylene group having three to six carbon atoms;

Y represents:
  an ethylene or methylene group or a direct bond (methylene is preferred)
  the bond represented by     is a single or double bond or, when $R^1$ represents a formyl group, represents a double bond; and
  n is an integer from 1 to 6;
wherein all alkyl groups and moieties, including those in alkoxy, alkoxycarbonyl and alkanoyl groups, can be straight-chain or branched, and, unless otherwise specified, contain one to four carbon atoms, and stereoisomers and salts thereof.

It is to be understood that, in this specification, including the accompanying claims, alkylene chains represented by $-(CH_2)_n-$ (or $-(CH_2)_m-$, hereinafter) may be straight- or branched-chain.

Particularly important classes of compounds of formula I include those which exhibit one or more of the following features:

(i) $R^1$ represents hydrogen or a cyano, carboxyl, formyl or alkoxycarbonyl group; or a group of the formula $-(CH_2)_nOR^2$, $-(CH_2)_nSR^2$, $-(CH_2)_nN(R^2)_2$, $-CH=CHR^3$, or $-CH=NOR^4$, preferably hydrogen or a cyano, carboxyl, formyl, methoxycarbonyl, ethoxycarbonyl or hydroxymethyl group, or an optionally substituted phenoxymethyl, e.g. phenoxymethyl, hydroxyphenoxymethyl or nitrophenoxymethyl, group, a phenylthiomethyl group, an optionally substituted phenylvinyl, e.g. fluorostyryl, group, an optionally substituted phenoxyiminomethyl, e.g. a fluorophenoxyiminomethyl group, a benzyloxyiminomethyl group, an optionally substituted alkoxyiminomethyl, for example a dihydroxyalkoxyiminomethyl, e.g. dihydroxypropoxyiminomethyl group, or an aminomethyl, benzoyloxymethyl or acetoxymethyl group;

(ii) $R^2$ represents hydrogen or an alkanoyl, aryl or arylCO- group, preferably hydrogen or an optionally substituted phenyl, e.g. hydroxyphenyl or nitrophenyl, group or a benzoyl or acetyl group;

(iii) $R^3$ represents an aryl, preferably optionally substituted phenyl, e.g. fluorophenyl, group;

(iv) $R^4$ represents an aryl or arylalkyl group; or an alkyl group substituted by one or more hydroxy groups, preferably an optionally substituted phenyl, e.g. fluorophenyl, group, or an optionally substituted phenylmethyl group, e.g. phenylmethyl;

(v) "aryl" indicates a phenyl group, which may be substituted by one or more substituents selected from halogen atoms and hydroxy and nitro groups;

(vi) Y represents a methylene group;

(vii) n is one;

(viii) R is methyl; and (ix) A is pyrid-3-yl or quinolin-3-yl; the other symbols being as hereinbefore defined, and their stereoisomers and pharmaceutically acceptable salts.

The presence of an exocyclic olefinic group =CHR$^1$ or a group —CH$_2$R$^1$ on the ring creates an isomeric centre in the molecule which in association with the adjacent asymmetric ring carbon atom leads to 4 stereoisomers which, optionally, can be separated into 2 racemic pairs. When a group —CH$_2$R$^1$ is present the racemic pair and enantiomers in which the —CH$_2$R$^1$ and —CSNHR groups are in the trans relationship are preferred. In certain cases the substituents A, R and R$^1$ can also contribute to stereoisomerism. All such forms are embraced by the present invention.

Particularly important compounds of the present invention include the following:

A (±)-2—Cyanomethylene-N-methyl-1-(pyrid-3-yl)-cyclohexane carbothioamide

B (±)-2-Formylmethylene-N-methyl-1-(pyrid-3-yl)-cyclohexane carbothioamide

C (±)-2—Cyanomethylene-N-methyl-1-(quinolin-3-yl)-cyclohexane carbothioamide

D (±)-2-Formylmethylene-N-methyl-1-(quinolin-3-yl)cyclohexane carbothioamide

E (±)-2-(2-Hydroxyethylidene)-N-methyl-1-(quinolin-3-yl)cyclohexane carbothioamide F (±)-trans/cis-2-Ethoxycarbonylmethylene-N-methyl-1-(quinolin-3-yl)cyclohexane carbothioamide G (±)-trans-2-Ethoxycarbonylmethylene-N-methyl-1-(quinolin-3-yl)cyclohexane carbothioamide H (±)-2-(2-Hydroxyethylidene)-N-methyl-1-(pyrid-3-yl)cyclohexane carbothioamide I (±)-2—Carboxymethylene-N-methyl-1-(quinolin-3-yl)cyclohexane carbothioamide J (±)-2-(2-Phenoxyethylidene)-N-methyl-1-(pyrid-3-yl)cyclohexane carbothioamide K (±)-2-(2-(4-Hydroxyphenoxy)ethylidene)-N-methyl-1-(pyrid-3-yl)cyclohexane carbothioamide L (±)-2-(2-(4-Nitrophenoxy)ethylidene)-N-methyl-1-(pyrid-3-yl)cyclohexane carbothioamide M (±)-2-(2-Phenylthioethylidene)-N-methyl-1-(pyrid-3-yl)cyclohexane carbothioamide N (±)-2-(4-Fluorostyryl)methylene-N-methyl-1-(pyrid-3-yl)cyclohexane carbothioamide O (±)-2-Formylmethylene-N-methyl-1-(pyrid-3-yl)-cyclohexane carbothioamide syn/anti-4-fluorobenzyloxime P (±)-2-Formylmethylene-N-methyl-1-(pyrid-3-yl)-cyclohexane carbothioamide syn/anti-2,3-dihydroxypropyloxime Q (±)-2-Methylene-N-methyl-1-(pyrid-3-yl)cyclohexane carbothioamide R (±)-trans-2-Cyanomethyl-N-methyl-1-(quinolin-3-yl)cyclohexane carbothioamide S (±)-trans-2-Cyanomethyl-N-methyl-1-(pyrid-3-yl)cyclohexane carbothioamide T (±)-trans-2-(2-Hydroxyethyl)-N-methyl-1-(pyrid-3-yl)cyclohexane carbothioamide U (±)-trans-2-[2-Aminoethyl)-N-methyl-1-(pyrid-3-yl)cyclohexane carbothioamide V (±)-trans-2-Methoxycarbonylmethyl-N-methyl-1-(pyrid-3-yl)cyclohexane carbothioamide W (±)-trans-2-Formylmethyl-N-methyl-1-(pyrid-3-yl)cyclohexane carbothioamide syn/anti-benzyloxime X (±)-trans-2-benzoyloxyethyl-N-methyl-1-(pyrid-3-yl)cyclohexane carbothioamide Y (±)-trans-2-acetoxyethyl-N-methyl-1-(pyrid-3-yl)cyclohexane carbothioamide as well as their stereoisomeric forms and pharmaceutically acceptable salts thereof.

Letters A to Y are allocated to compounds for ease of reference in other parts of the specification.

The compounds have valuable pharmacological properties, in particular properties which are indicative of utility in the treatment and/or prophylaxis of disorders associated with:

(1) vascular smooth muscle contraction including hypertension and other cardiovascular disorders such as congestive heart failure, and conditions associated with tissue ischaemia such as angina, peripheral vascular disease and cerebrovascular disease;

(2) respiratory smooth muscle contraction including reversible airways obstruction and asthma;

(3) contraction of smooth muscle of gastrointestinal tract, urinary bladder and uterus, including peptic ulcers, irritable bowel syndrome and diverticular disease; irritable bladder syndrome; and premature labour.

The compounds also have utility in the inhibition of head hair loss associated with male pattern baldness, by topical application.

For example, compounds of general formula (I) were submitted to:

Vaso-relaxant Activity Tests

The test methods used were adapted from those described by Winslow et al. [Eur.J.Pharmacol., 131, 219–228 (1986)] and Karaki [J.Pharmacol. Methods, 18, 1–21 (1987)] for differentiating vaso-relaxant activity.

Test A: Activity Against Contractions Induced by Low K$^+$ Concentrations in the Isolated Rat Aorta Thoracic aorta was removed from rat and transverse strips, denuded of endothelium, were suspended in a bath containing Krebs solution. The tension was recorded and a contraction induced by addition of 20 mM K$^+$ (potassium ion) to the bathing solution. The test compound was added to the bath as a solution in increasing cumulative concentration. The concentration in the bathing solution of the test compound which reduced the K$^+$-induced contraction by 90% was determined and expressed in $\mu$M as the effective concentration EC$_{90}$), given in Table 1.

TABLE 1

| Compound | Activity Test A EC$_{90}$ $\mu$M |
| --- | --- |
| A | 10 |
| B | 10 |
| C | 0.2 |
| D | 3 |
| E | 3 |
| F | 0.3 |
| G | 0.3 |
| H | 10 |
| J | 0.07 |
| K | 0.3 |
| L | 0.1 |
| M | 0.003 |
| N | 0.03 |
| O | 0.1 |
| P | 3 |
| Q | 3 |
| R | 0.1 |
| S | 0.3 |
| T | 1.7 |
| V | 0.03 |
| W | 0.03 |

Test B: Activity Against Contractions Induced by High K$^+$ Concentrations in Isolated Rat Aorta The test method was as in Test A with the exception that contractions were induced by addition of 60 mM K+ to the bathing solution. The cumulative addition of the solutions of the test compound was conducted and the concentration in the bath reducing the K+-induced contraction by 90 mM % was found and expressed as the $EC_{90}$. For each compound tested it was greater than 30 μM.

The compounds of general formula (I) can be prepared by the application and adaptation of known methods, for example as hereinafter identified. By the term "known methods" as used in this specification is meant methods heretofore used or described in the literature.

According to a feature of the present invention, the compounds of formula (I), wherein $R^1$ represents cyano or alkoxycarbonyl,  represents a double bond and the other symbols are as hereinbefore defined, may be prepared by the reaction of a compound of general formula (II), wherein A, Y and R are as hereinbefore defined, with a phosphonate of general formula:

$$(R^7O)_2P(O)CH_2R^{1'} \qquad (III)$$

where $R^7$ represents an alkyl group of 1 to 4 carbon atoms, preferably a methyl or ethyl group, and $R^{1'}$ represents cyano or alkoxycarbonyl. The reaction is generally carried out in the presence of a base, preferably sodium hydride, in an ethereal solvent (e.g. tetrahydrofuran) and preferably at a temperature of from 20° C. to 100° C.

Compounds of formula (I), wherein $R^1$ is formyl and the other symbols are as hereinbefore defined, can be obtained from compounds of formula (I), wherein $R^1$ is cyano,  represents a double bond, and the other symbols are as hereinbefore defined, by reaction with a complex metal reducing agent, preferably a dialkylaluminium hydride (e.g. diisobutylaluminium hydride) in a dry, inert, organic solvent, for example a mixture of an ether (e.g. tetrahydrofuran) and an aromatic hydrocarbon (e.g. toluene) at a temperature from −80° C. to +30° C.

Compounds of formula (I), wherein $R^1$ is hydroxymethyl and the other symbols are as hereinbefore defined, can be obtained from compounds of formula (I), wherein $R^1$ is formyl and the other symbols are as hereinbefore defined, or from compounds of formula (XXXIV) wherein $R^{11}$ represents a p-methoxybenzyl group and the other symbols are as hereinbefore defined, by reaction with a complex metal reducing agent, preferably a boron hydride (e.g. sodium borohydride) in an alcoholic solvent (e.g. methanol) at room temperature; when  represents a single bond the reaction can also be carried out with an aluminium alkoxide (e.g. aluminium isopropoxide) in an alcoholic solvent (e.g. isopropanol) at reflux.

Compounds of general formula (II), wherein A, Y and R are as hereinbefore defined may be prepared by the reaction of a compound of general formula (IV), wherein A and Y are as hereinbefore defined, with an isothiocyanate of the general formula:

$$R-N=C=S \qquad (V)$$

wherein R is as hereinbefore defined. The reaction is generally carried out in an anhydrous inert organic solvent such as tetrahydrofuran, dimethylformamide or hexamethylphosphoramide, or a mixture of these solvents, at a temperature from −80° C. to +50° C., in the presence of an inorganic base such as potassium tert.-butoxide, or an organo-lithium derivative such as n-butyllithium, or of sodium hydride.

Compounds of formula (IV), wherein A is as hereinbefore defined and Y is a methylene or ethylene group, can be made via a dehydrobromination/rearrangement reaction of compounds of formula (VI), wherein A and Y are as defined above. This may be initiated by a bromide extracting agent such as a silver salt (e.g. silver perchlorate) and carried out in an inert anhydrous solvent (for example an ether such as tetrahydrofuran).

Compounds of formula (VI), wherein A and Y are as defined above, can be made by the addition of hypobromous acid across the double bond of compounds of formula (VII), wherein A and Y are as defined above. This may be done by reaction with a brominating agent (e.g. 1,3-dibromo-5,5-dimethylhydantoin) in an aqueous acidic medium, optionally in the presence of a co-solvent.

Compounds of formula (VII), wherein A and Y are as defined above, can be made via a coupling reaction between a phosphorane of formula (VIII) (typically made in situ by the reaction of a compound of formula (IX), wherein Y is as defined above and $R^8$ and Z are conventional groups present in a Wittig reagent and its phosphonium salt precursor [e.g. phenyl and bromine respectively] with a strong base, such as potassium t-butoxide, in an anhydrous solvent, such as tetrahydrofuran, preferably under an inert atmosphere) and a compound of formula:

$$A-CHO \qquad (X)$$

wherein A is as defined above.

Alternatively compounds of formula (IV), wherein Y is ethylene, methylene or a direct bond and A is as hereinbefore defined, can be made by the removal of methanol from compounds of formula (XI), wherein A and Y are as defined above. This is typically carried out in the presence of a strongly acidic agent (e.g. phosphorus pentoxide or sulphuric acid), optionally in a solvent (such as toluene) and at elevated temperature.

Compounds of formula (XI) can be made by reaction of a compound of formula:

$$A-Hal \qquad (XII)$$

wherein A is as defined above and Hal is a halogen, preferably bromine or chlorine atom, in the presence of a strong base, such as an alkyl lithium (e.g. butyllithium), with a compound of formula (XIII), wherein Y is as defined above, in an inert solvent such as an ether (e.g. diethyl ether) or a hydrocarbon (e.g. toluene).

According to a further feature of the invention, compounds of general formula (I), wherein $R^1$ is a cyano or alkoxycarbonyl group or a group of formula $-(CH_2)_nOR^2$, $-(CH_2)_2SR^2$ or $-CH=NOR^4$, as hereinbefore defined, or $-CH=CHR^{3'}$ wherein $R^{3'}$ represents hydrogen, an alkyl, alkanoyl, cyano, aryl, arylCO—, aryl$(CH_2)_n$—, or aryl(CH nCO—group; or an alkyl group substituted by an alkoxy group,  represents a double bond, R is preferably methyl, and the other symbols are as hereinbefore defined can be prepared from compounds of general formula (XIV), wherein A and Y are as defined above, $R^{1''}$ is a cyano or alkoxycarbonyl group or a group of formula $-(CH_2)_nOR^2$, $-(CH_2)_nSR^2$ or $-CH=NOR^4$, as hereinbefore defined, or $-CH=CHR^{3'}$ wherein $R^{3'}$ represents hydrogen, an alkyl, alkanoyl, cyano, aryl, arylCO—, aryl(CH$_2$)$_n$—, or aryl(CH$_2$)$_n$CO— group; or an alkyl group substituted by an alkoxy group, and R$^9$ is an alkyl group of 1 to 4 carbon atoms, by reaction with an alkylamine of general formula:

$$R-NH_2 \qquad (XV)$$

wherein R is as hereinbefore defined, and is preferably methyl. The reaction is generally carried out in an inert organic solvent such as tetrahydrofuran at room temperature and the amine is added usually in an alcoholic solution, preferably ethanol.

The dithioesters of formula (XIV), wherein Y, A and R$^9$ are as defined above and R$^{1''}$ is aryloxymethyl or arylthiomethyl, are prepared by a Mitsunobu reaction of alcohol of general formula (XVI), wherein Y, A and R$^9$ are as hereinbefore defined, using phenols or thiophenols of formula:

$$R^{10}-XH \qquad (XVII)$$

wherein R$^{10}$ is aryl and X is oxygen or sulphur. The reaction is carried out at room temperature in an inert organic solvent, preferably tetrahydrofuran, in the presence of triphenylphosphine and a dialkyl (e.g. di-isopropyl) azodicarboxylate.

Compounds of formula (XVI), wherein the various symbols are as hereinbefore defined, can be obtained from aldehydes of formula (XVIII) by reaction with a complex metal reducing agent, preferably a boron hydride (e.g. sodium borohydride) in an alcoholic solvent (e.g. methanol) at room temperature.

Compounds of formula (XVIII) may be obtained from cyanides of formula (XIX) by reaction with a complex metal reducing agent, preferably a dialkyl aluminium hydride (e.g. diisobutylaluminium hydride) in a dry, inert organic solvent, for example a mixture of an ether (e.g. tetrahydrofuran) and an aromatic hydrocarbon (e.g. toluene) at a temperature from −80° to 30° C.

The compounds of formula (XIX), wherein the various symbols are as hereinbefore defined, may be prepared by the reaction of a compound of formula (XX), wherein Y, A and R$^9$ are as hereinbefore defined, with a phosphonate of the general formula (III), wherein R$^7$ is as hereinbefore defined and R$^1$ is a cyano group, under the conditions described previously.

Compounds of formula (XX), wherein Y, A and R$^9$ are as hereinbefore defined may be prepared by the reaction of compounds of formula (IV), wherein Y and A are as hereinbefore defined, with carbon disulphide followed by reaction with an alkyl halide of formula:

$$R^9-X \qquad (XXI)$$

wherein R$^9$ is as hereinbefore defined and X is halogen, preferably iodine. The reaction is generally carried out in an anhydrous inert organic solvent such as tetrahydrofuran at a temperature from −80° C. to +50° C. in the presence of an organic base such as potassium tert.-butoxide, or an organo-lithium derivative such as butyllithium, or sodium hydride.

The dithioesters of formula (XIV), wherein the various symbols are as hereinbefore defined and R$^{1''}$ represents a group of the formula —CH=NOR$^4$, may be prepared by the reaction of a compound of formula (XVIII) with an acid addition salt of an optionally O-substituted hydroxylamine (preferably the hydrochloride), of the general formula:

$$NH_2-OR^4 \qquad (XXII)$$

wherein R$^4$ is as hereinbefore defined. The reaction is generally carried out in the presence of an organic base e.g. pyridine which may serve as the solvent, in an otherwise inert organic solvent at a temperature from 0° C. to 40° C.

According to a further feature of the present invention compounds of formula (I), wherein R$^1$ represents a carboxy group and the other symbols are as hereinbefore defined, may be prepared by the reaction of a compound of formula (I), wherein R$^1$ is an alkoxycarbonyl, preferably ethoxycarbonyl, group and the other symbols are as hereinbefore defined, with an inorganic aqueous base, preferably sodium hydroxide at room temperature.

According to a further feature of the present invention, compounds of formula (I), wherein R$^1$ represents a group of formula —CH=CHR$^{3''}$, wherein R$^{3''}$ represents hydrogen, alkyl, aryl, aryl(CH$_2$)$_n$—, alkanoyl, arylCO—, or aryl(CH$_2$)$_n$CO—, or alkyl substituted by hydroxy or alkoxy and the other symbols are as hereinbefore defined may be prepared from compounds of formula (I), wherein R$^1$ is formyl, or (XXXIV), the other symbols being as hereinbefore defined, via a coupling reaction with a phosphorane of formula:

$$R^{3''}-CH=PPh_3 \qquad (XXIII)$$

wherein Ph represents phenyl and R$^{3''}$ is as hereinbefore defined, provided that when R$^{3''}$ represents alkyl substituted by hydroxy, the hydroxy group is protected, for example as the tetrahydropyranyloxy group, and subsequently deprotected.

The phosphorane is typically made by reaction of a compound of formula:

$$(R^{3''}-CH_2-PPh_3)^+ \, Z^- \qquad (XXIV)$$

wherein R$^{3''}$, Ph and Z are as hereinbefore defined, with a strong base, such as butyllithium, in an anhydrous solvent such as tetrahydrofuran, preferably under an inert atmosphere at room temperature.

According to a further feature of the invention, compounds of formula (I), wherein R$^1$ represents a group of formula —CH=CHR$^3$, in which R$^3$ is alkyl substituted by carboxy, and the other symbols are as hereinbefore defined, can be prepared by oxidation, by known methods, of the corresponding compounds of formula (I), in which R$^3$ represents alkyl substituted by hydroxy.

Compounds of formula (I), wherein R represents a group of formula —CH=CHR$^3$, wherein R$^3$ represents carboxyl, and the other symbols are as hereinbefore defined, can be prepared by oxidation, in known manner, of the corresponding formyl compound.

The formyl compound can be prepared by the procedure described above for the preparation of compounds in which R$^3$ represents alkanoyl.

Compounds of formula (I), wherein R$^1$ represents a group of formula —CH=CHR$^3$, wherein R$^3$ represents carbamoyl, can be prepared by the reaction of the corresponding compound in which R$^3$ represents carboxyl, or the acid chloride thereof, with ammonia. The reaction may be carried out as hereinafter described for the reaction of ammonia with a compound of formula (I), in which R$^1$ is carboxy.

Compounds of formula (I) wherein $R^1$ represents a group of formula $-CH=CHR^3$, wherein $R^3$ represents cyano can be prepared by dehydration, in known manner, of the corresponding compound in which $R^3$ represents carbamoyl.

Compounds of formula (I), wherein $R^1$ represents a group of formula $-CH=CHR^3$, wherein $R^3$ represents cyano, and the other symbols are as hereinbefore defined, may be prepared by the reaction of compounds of formula (I) or (XXXIV), wherein $R^1$ is formyl and the other symbols are as hereinbefore defined, with a compound of formula:

$(R^7O)_2P(O)CH_2CN$ (IIIA)

wherein $R^7$ is hereinbefore defined, under conditions similar to those described for the reaction of a compound of formula (II) with a phosphonate of formula (III).

The resulting compounds of formula (I), wherein $R^1$ represents a group of formula $-CH=CHR^3$, wherein $R^3$ is cyano can be converted into the corresponding compounds wherein $R^3$ is carbamoyl or carboxy by progressive hydrolysis in known manner.

According to a further feature of the invention, compounds of formula (I), wherein $R^1$ is carbamoyl or a group of formula $CONHR^5$, as hereinbefore defined, and the other symbols are as hereinbefore defined, can be prepared by the reaction of the corresponding acid chloride of formula (XXV), hereinafter depicted, with ammonia, or an amine of formula:

$R^5-NH$ (XXVI)

wherein $R^5$ is as hereinbefore defined, in the presence of an acid acceptor, for example a tertiary amine such as triethylamine, or an inorganic base, such as sodium bicarbonate, preferably in an anhydrous, inert solvent, e.g. chloroform or acetone, and preferably at a temperature of from $-30°$ C. to $30°$ C.

The acid chloride of formula (XXV) can be made from the corresponding acid (the compound of formula (I), wherein $R^1$ is carboxyl) with a conventional reagent, such as thionyl chloride, in the absence or, preferably, in the presence of an inert solvent, such as toluene or tetrahydrofuran, at from room temperature to reflux.

According to a further feature of the invention, compounds of formula (I), wherein $R^1$ represents a group of formula $COR^6$ and the other symbols are as hereinbefore defined, can be prepared by the reaction of an acid chloride of formula (XXV) with an organocadmium compound of formula:

$Cd(R^6)_2$ (XXVII)

wherein $R^6$ is as hereinbefore defined, under conventional reaction conditions in an inert solvent, such as tetrahydrofuran.

The organocadmium compounds of formula (XXVII) can be made by the reaction of a cadmium halide, for example the chloride, with the corresponding Grignard reagent of formula:

$R^6MgBr$ (XXVIII)

in an inert solvent, for example diethyl ether or tetrahydrofuran.

According to a further feature of the invention, compounds of formula (I), wherein $R^1$ is alkyl, and the other symbols are as hereinbefore defined, can be prepared from the corresponding compounds of formula (I), wherein $R^1$ is formyl or $COR^6$, or (XXXIV), by reaction with hydrazine and an inorganic base, preferably sodium or potassium hydroxide, in a high boiling organic solvent, e.g. diethylene glycol, at elevated temperature, preferably at reflux.

According to a further feature of the invention, compounds of formula (I), wherein $R^1$ is a group of formula wherein L is $-OR^2$, $-SR^2$ or $-N(R^2)_2$, m is an integer from 2 to 6 and the other symbols are as hereinbefore defined, can be made by the reduction of a ketone of formula (XXIX), hereinafter depicted, using hydrazine and a strong base, under conditions similar to those described above.

Compounds of formula (XXIX) can be made from the acid chloride of formula (XXV) and the appropriate organocadmium compound of formula:

$Cd[(CH_2)_{m-1}L]_2$ (XXX)

under conditions similar to those described above.

The organocadmium compound can similarly be made from the corresponding Grignard reagent of formula:

$BrMg[(CH_2)_{m-1}L]$ (XXXI)

again under conditions similar to those described above.

If the group L contains an active hydrogen (e.g. if $R^2$ is hydrogen) then this should be suitably protected as necessary during the above reaction sequences involving organometallic species and deprotection should take place at a later stage. For example, if the active hydrogen is in a hydroxyl group it can be protected by the formation of the tetrahydropyranyl ether, if it is a thiol group by the use of a p-methoxybenzyl group and if it is an amino o imino group by formation of a t-butoxycarbonyl group. In each instance protection and later deprotection can be carried out by conventional means.

According to a further feature of the invention, compounds wherein $R^1$ is $-CH_2NHR^{2'}$ or $-CH_2N(R^{2'})_2$, $R^{2'}$ represents an alkyl or aryl$(CH_2)_n-$ group and the other symbols are as hereinbefore defined, can be prepared by reaction of compounds of general formula (I) wherein $R^1$ is aminomethyl with a corresponding alkyl or alkylaryl halide, in the presence or absence of an inert organic solvent, such as an aromatic hydrocarbon (e.g. benzene or toluene), a halogenated solvent (e.g. chloroform or dichloromethane), an ether (e.g. tetrahydrofuran), or dimethylformamide, generally at a temperature from $0°$ C. to the reflux temperature of the reaction mixture.

According to a further feature of the invention, compounds of formula (I), wherein $R^1$ is aminomethyl, and the other symbols are as hereinbefore defined, can be prepared from the corresponding compounds wherein $R^1$ is cyano by reduction by known methods, for example by reaction with a complex metal reducing agent, such as an aluminium hydride (e.g. lithium aluminium hydride) in a dry organic solvent, such as an ether (e.g. tetrahydrofuran) at elevated temperature, preferably from $40°$ to $80°$ C.

According to a further feature of the invention, compounds of formula (I), wherein $R^1$ is the group $-CH_2SH$ and the other symbols are as hereinbefore defined, can be made by the hydrolysis of the corresponding thiolacetate ester of formula (XXXII), hereinafter depicted, generally by reaction with an aqueous base in an an organic solvent, for example ethanolic ammonia, at room temperature.

The ester of formula (XXXII) can be made by the reaction of the corresponding alcohol (i.e. the compound of formula (I), wherein $R^1$ is hydroxymethyl), by a reaction under Mitsunobu conditions in the presence of thioacetic acid. The reaction is typically carried out in an inert solvent, preferably tetrahydrofuran, and in the presence of triphenylphosphine and a dialkyl (e.g. diisopropyl) azodicarboxylate, at room temperature.

According to a further feature of the invention, compounds of formula (I), wherein $R^1$ is a group of formula $-CH_2$ S-alkyl, $-CH_2S-(CH_2)_n$aryl, $-CH_2O$-alkyl or $-CH_2O-(CH_2)_n$ aryl and the other symbols are as hereinbefore defined, are prepared from the corresponding alcohol or thiol of formula (I), by reaction with the appropriate alkyl or aralkyl halide, preferably bromide, generally in the presence of a strong base such as sodium hydride, in an inert organic solvent, such as tetrahydrofuran or dimethylformamide, at a temperature up to the reflux temperature of the reaction mixture.

According to a further feature of the invention, compounds of formula (I), wherein $R^1$ is a group of formula $-(CH_2)_nOR^2$ or $-(CH_2)_nSR^2$ wherein $R^2$ is alkanoyl or arylCO— and the other symbols are as hereinbefore defined, are made from the corresponding compounds wherein $R^2$ is hydrogen, optionally with the thioamide group suitably protected, as hereinafter described, by reaction with the appropriate acyl or aryl halide, preferably the chloride, in an inert organic solvent such as toluene or dichloromethane at a temperature from 0° to 25° C. optionally in the presence of a suitable activator, e.g. 4-dimethylaminopyridine.

According to a further feature of the invention, the compounds of formula (I), wherein A, R and Y are as hereinbefore defined, represents a double bond and $R^1$ is hydrogen, can be prepared by the dehydration of an alcohol of formula (XXXIII), hereinafter depicted. This reaction is carried out under Mitsunobu conditions, in an inert solvent in the presence cf triphenylphosphine and a dialkyl (e.g. diisopropyl) azodicarboxylate and at room temperature.

The compounds of formula (XXXIII) can be made by the reaction of a ketone of formula (II) with methylmagnesium bromide, in an inert solvent such as diethyl ether or tetrahydrofuran at temperatures below 10° C.

According to a feature of the present invention, compounds of formula (I), wherein $R^1$ is cyano, represents a single bond and A, Y and R are as hereinbefore defined, may be prepared by the reduction of the corresponding compounds of general formula (I), wherein represents a double bond, with a complex metal reducing agent, such as an aluminium hydride (e.g. lithium aluminium hydride) in a dry inert organic solvent, such as an ether (e.g. tetrahydrofuran) at room temperature.

This reaction preferentially gives the reduced product (I) in which the —CSNHR group bears a trans relationship to the —CH$_2$CN group.

According to a further feature of the invention, compounds of formula (I), wherein $R^1$ is the group —CH=NOR$^4$, as hereinbefore defined, and the other symbols are as hereinbefore defined, can be prepared from the corresponding compounds of formula (I) wherein $R^1$ is formyl or (XXXIV) by reaction with an acid addition salt of an optionally O-substituted hydroxylamine (preferably the hydrochloride) of formula (XXII), wherein $R^4$ is as hereinbefore defined, the thioamide group —CSNHR being in the protected form prior to the reaction and subsequently deprotected. The reaction is generally carried out in the presence of an organic base, e.g. pyridine, which may also serve as solvent, in an otherwise inert solvent at a temperature from 0° C. to 40° C.

According to a further feature of the invention, compounds of formula (I), wherein $R^1$ is a group of formula —CH$_2$XR$^{2''}$ wherein $R^{2''}$ represents aryl and X is as hereinbefore defined, is a single bond and the other symbols are as hereinbefore defined, can be prepared from the corresponding compounds of formula (I), wherein $R^1$ is —CH$_{20}$ H, by conversion of the hydroxy group in $R^1$ to a suitable leaving group, for example by conversion of the hydroxymethyl group to a bromomethyl or p-toluenesulphonyloxymethyl group, e.g. by reaction with phosphorus tribromide or p-toluenesulphonyl chloride, followed by reaction with a compound of the formula MXR$^{2'}$, wherein $R^{2'}$ and X are as hereinbefore defined and M represents an alkali metal atom, e.g. sodium, under conventional reaction conditions, the thioamide group —CSNHR being protected prior to the reaction and subsequently deprotected as described hereinafter.

According to a further feature of the invention, compounds of formula (I), wherein $R^1$ is alkoxycarbonyl and the other symbols are as hereinbefore defined, can be prepared from the corresponding compounds of formula (I), wherein $R^1$ is cyano, with an alcohol in the presence of hydrogen chloride, optionally in a cosolvent, such as an ether (e.g. diethyl ether), at room temperature.

According to a further feature of the invention, compounds of formula (I), wherein $R^1$ is carboxyl and the other symbols are as hereinbefore defined, can be prepared from the corresponding compounds of formula (I), wherein $R^1$ is cyano or alkoxycarbonyl, by hydrolysis with an inorganic aqueous base, preferably sodium hydroxide, at room temperature, or under gentle heating.

Alternatively according to the invention, the compounds of formula (I), wherein $R^1$ is carboxyl and the other symbols are as hereinbefore defined, can be prepared from the corresponding compounds of formula (I), wherein $R^1$ is formyl, or (XXXIV) using, for example silver oxide, sodium chlorite or potassium dichromate and pyridine, under conventional reaction conditions.

According to a further feature of the invention, compounds of formula (I), wherein A, R and Y are as hereinbefore defined, represents a single bond and $R^1$ is hydrogen, can be prepared from the corresponding compounds in which represents a double bond by catalytic hydrogenation using for example a supported platinum or palladium catalyst, Raney nickel or a homogeneous catalyst, e.g. Wilkinson's catalyst.

According to a further feature of the invention, compounds of formula (I), wherein $R^1$ is CONHR$^5$ or CONH$_2$ and the other symbols are as hereinbefore defined, are prepared by the reaction of a compound of formula (I), wherein $R^1$ is carboxy and the other symbols are as hereinbefore defined, with a compound of formula (XXV), or with ammonia, in a solvent, such as dichloromethane, and in the presence of a coupling agent, such as dicyclohexylcarbodiimide, typically at room temperature; the reaction with ammonia can also be carried out in aqueous solution either at room temperature or under heat in a closed pressure vessel.

According to a further feature of the invention, compounds of formula (I), wherein A, R and Y are as hereinbefore defined and $R^1$ is carbamoyl, are prepared by the mild hydrolysis of a compound of formula (I), wherein A, R and Y are as hereinbefore defined and $R^1$ is cyano.

During a number of the above reaction sequences it is desirable or essential to use as starting material a compound wherein the thioamide group is protected, for example in the form of a group of formula —C(=N-R)—$SR^{11}$ wherein R and $R^{11}$ are as hereinbefore defined. These can be prepared, for example, by reaction with p-methoxybenzyl chloride in an anhydrous organic solvent, such as tetrahydrofuran or dimethylformamide, at a temperature from $-20°$ C. to $20°$ C. in the presence of a base such a potassium t-butoxide, an organolithium compound (such as n-butyl lithium) or sodium hydride in order to form the said group of formula —C(=NR)—$SR^{11}$. Compounds of formula XXXIV are examples of such protected compounds. The thioamide group can then later be regenerated by acidification or by deprotection in acidic media, preferably formic acid at from $5°$ to $20°$ C. or trifluoroacetic acid and anisole at from $0°$ to $5°$ C.

Compounds of formulae (III), (IIIA), (V), (IX), (X), (XII), (XIII), (XV), (XVII), (XXI), (XXII), (XXIV), (XXVI), (XXVIII) and (XXXI) can be made by application or adaptation of known methods or are readily available.

It is to be understood that the conversion, for example by known methods, such as those hereinbefore described, of one compound of general formula (I) into another compound of formula (I) constitutes a feature of the present invention.

It will be understood that it may be desirable to change one or more of the substituents at an appropriate stage during the synthesis of the compounds of the invention. For example, the compounds of general formula (I) wherein A represents a phenyl group substituted by a carbamoyl group may be alternatively prepared from the corresponding compounds of general formula (I) wherein A represents a phenyl group substituted by a cyano group by the application or adaptation of known methods for such conversion.

By the term "pharmaceutically acceptable salts" as used in this specification is meant salts the anions or cations of which are relatively innocuous to the animal organism when used in therapeutic doses so the beneficial pharmaceutical properties of the parent compounds of general formula (I) capable of forming salts are not vitiated by side-effects ascribable to those anions or cations.

Suitable acid addition salts for use in pharmaceuticals may by selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-β-hydroxynaphthoates, gentisates and di-p-toluoyltartrates.

As well as being useful in themselves as active compounds, salts of the compounds of general formula (I) capable of forming salts with bases are useful for the purposes of purification of the parent compounds of general formula (I), for example by exploitation of the solubility differences between the salts and the parent compounds, by techniques well known to those skilled in the art.

Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmenthylamine) salts.

It is to be understood that, where in this specification reference is made to compounds of formula (I), it is intended to refer also, where the context so permits, to their pharmaceutically acceptable salts.

The thioformamide derivatives of general formula (I) obtained by the aforedescribed processes can be purified by the usual physical methods, in particular crystallisation and chromatography, especially to resolve mixtures of enantiomers using a chiral column.

-continued

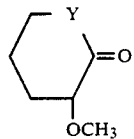 (XIII)

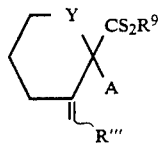 (XIV)

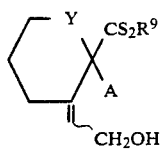 (XVI)

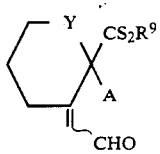 (XVIII)

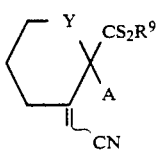 (XIX)

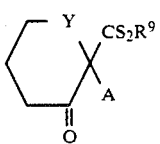 (XX)

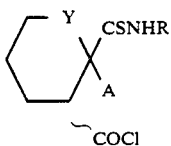 (XXV)

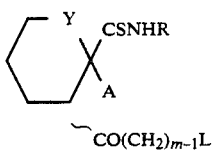 (XXIX)

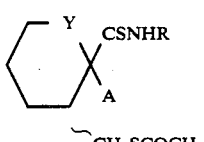 (XXXII)

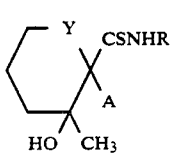 (XXXIII)

-continued

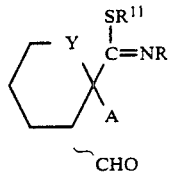 (XXXIV)

The following Examples illustrate the preparation of compounds according to the present invention.

All N.M.R spectra were recorded at 200 MHz. The chemical shifts are expressed in ppm relative to tetramethylsilane. Abbreviations in the text are as follows:

s=singlet, d=doublet, t=triplet, q=quartet, dd=doublet of doublets, ddd=doublet of doublets of doublets, dt=doublet of triplets, m=multiplet, c=unresolved complex peak, br=broad signal.

The expression "m/z" indicates the peak assigned to the molecular ion in the mass spectrum.

EXAMPLE 1

Compound A

A solution of diethyl cyanomethylphosphonate (215 mg, 1.2 mmol) at room temperature in dry tetrahydrofuran (20 ml) was treated with a 60% oil dispersion of sodium hydride (40 mg, 1mmol). After 15 mins at room temperature (±)-N-methyl-2 -oxo-1-(pyrid-3 -yl)cyclohexane carbothioamide (245 mg, 1mmol) was added and the resulting solution stirred for 3 hours at room temperature. Ethyl acetate (50 ml) and then water (50 ml) were added to the reaction mixture. The layers were separated and the organics washed with water (50 ml). The organic extract was dried over magnesium sulphate and concentrated in vacuo to give a crude gum. Purification by flash chromatography, eluting with a 1:1 (v/v) mixture of ethyl acetate/hexane gave (±)-2 -cyanomethylene-N-methyl-1-(pyrid-3 -yl)cyclohexane carbothioamide as a colourless gum (190 mg, 0.7 mmol). Trituration with ether yielded a white solid (190 mg, 0.7 mmol), m.p. 182°–183° C.;

[N.M.R (CDCl$_3$): 1.47–1.78 (c, 2H), 1.78–2.00 (c, 2H), 2.20–2.38 (m, 1H), 2.46–2.64 (m, 1H), 2.82–2.96 (m, 1H), 3.06–3.24 (m, 1H), 3.22–3.26 (d, 3H), 3.94 (s, 1H), 7.26–7.36 (m, 1H), 7.48–7.64 (m, 2H), 8.48–8.52 (m, 1H), 8.52–8.58 (m, 1H)

Found: C, 66.6; H, 6.3; N, 15.7%; Calculated for C: C, 66.4; H, 6.3; N, 15.5%. m/z=271].

EXAMPLE 2

Compound B

A solution of (±)-2 -cyanomethylene-N-methyl-1-(pyrid-3 -yl)cyclohexane carbothioamide (1.3 g, 4.8 mmol) in dichloromethane (30 ml) was cooled to −20° C. and treated with a 1 M solution of diisobutylaluminium hydride in toluene (10.6 ml, 10.6 mmol). The mixture was allowed to warm to room temperature over 2 hours. Dichloromethane (50 ml) was added to the reaction mixture followed by an aqueous solution of Rochelle salt (sodium potassium tartrate) (50 ml). The layers were separated and the organic layer was washed with an aqueous solution of Rochelle salt (50 ml). The organic extract was dried over magnesium sulphate and concentrated in vacuo to give a crude gum which was purified by flash chromatography over silica gel, eluting with a 4:1 (v/v) mixture of ethyl acetate/hexane to give (±)-2 -formylmethylene-N-methyl-1-

(pyrid-3-yl)cyclohexane carbothioamide as a white foam (230 mg, 0.84 mmol);

[N.M.R. (CDCl$_3$): 1.64–1.82 (c, 2H), 1.82–2.04 (c, 2H), 2.30–2.46 (m, 1H), 2.46–2.70 (m, 1H), 3.10–3.20 (c, 2H), 3.20–3.28 (d, 3 H), 5.66–5.72 (d, 1H), 7.28–7.36 (m, 1H), 7.36–7.48 (br s, 1H), 7.52–7.60 (m, 1H), 8.48–8.52 (m, 1H), 8.52–8.58 (m, 1H), 10.06–10.12 (d, 1H).

Found: C, 65.4; H, 6.8; N, 10.0%; Calculated for C: $C_{15}H_{18}N_2OS$: C, 65.7; H, 6.6; N, 10.2%. m/z=274].

EXAMPLE 3

Compound C

A solution of diethyl cyanomethylphosphonate (2.97 g, 16.76 mmol) at room temperature in dry tetrahydrofuran (100 ml) was treated with a 60% oil dispersion of sodium hydride (670 mg, 16.76 mmol). After 30 mins at room temperature ($\pm$)-N-methyl-2-oxo-1-(quinolin-3-yl)cyclohexane carbothioamide (5 g, 16.76 mmol) was added in one portion and the resulting solution stirred for 3 hours at room temperature. Ethyl acetate (200 ml) and then water (200 ml) were added to the reaction mixture. The layers were separated and the organic extract was dried over magnesium sulphate. Concentration in vacuo yielded a brown gum which was purified by flash chromatography over silica gel, eluting with a 3:7 (v/v) mixture of ethyl acetate/hexane to give ($\pm$)-2-cyanomethylene-N-methyl-1-(quinolin-3-yl)cyclohexane carbothioamide (2.8 g, 8.72 mmol) as a white solid, m.p. 108°–111° C.;

[N.M.R. (CDCl$_3$) 1.60–2.00 (c, 4 H), 2.38–2.52 (c, 2H), 2.80–2.96 (m, 1H), 3.10–3.22 (m, 1H), 3.22–3.26 (d, 3 H), 5.08 (s, 1H), 7.26–7.42 (br s, 1H), 7.58–7.64 (dd, 1H), 7.70–7.84 (m, 2H), 7.82–7.86 (d, 1H), 8.06–8.12 (dd, 1H), 8.76–8.80 (d, 1H).

Found: C, 71.1; H, 6.15; N, 12.7; S, 9.5%; Calculated for $C_{19}H_{19}N_3S$: C, 71.0; H, 5.9; N, 13.1; S, 10.0%].

EXAMPLE 4

Compound D

A solution of ($\pm$)-2-cyanomethylene-N-methyl-1-(quinolin-3-yl)cyclohexane carbothioamide (1 g, 3.1 mmol) in dichloromethane (25 ml) was cooled to $-20°$ C. and treated with a 1 M solution of diisobutylaluminium hydride in toluene (3.1 ml, 3.1 mmol). The mixture was allowed to warm to 10° C. over 90 mins. Dichloromethane (50 ml) was added to the reaction mixture followed by an aqueous solution of Rochelle salt (50 ml). The layers were separated and the organic layer was washed with an aqueous solution of Rochelle salt (50 ml). The organic extract was dried over magnesium sulphate and concentrated in vacuo to yield a yellow oil. Purification by flash chromatography over silica gel, eluting with a 1:1 (v/v) mixture of ethyl acetate/hexane yielded ($\pm$)-2-formylmethylene-N-methyl-1-(quinolin-3-yl)cyclohexane carbothioamide (300 mg, 0.93 mmol) as a pale yellow solid, m.p. 149°–151° C.;

[N.M.R. (CDCl$_3$): 1.60–2.04 (c, 4H), 2.46–2.74 (c, 2H), 3.10–3.24 (c, 2H), 3.24–3.28 (d, 3H), 5.68–5.74 (d, 1H), 7.44–7.60 (br s, 1H), 7.52–7.64 (m, 1H), 7.70–7.82 (m, 2H), 7.90–7.96 (d, 1H), 8.04–8.12 (dd, 1H), 8.98–9.02 (d, 1H), 10.10–10.16 (d, 1H)

Found: C, 70.1; H, 6.3; N, 8.1%; Calculated for $C_{19}H_{20}N_2OS$: C, 70.4; H, 6.2; N, 8.6%].

EXAMPLE 5

Compound E

A solution of ($\pm$)-2-formylmethylene-N-methyl-1-(quinolin-3-yl)cyclohexane carbothioamide (150 mg, 0.46 mmol) at room temperature in methanol (5 ml) was treated with sodium borohydride (20 mg, 0.5 mmol). The mixture was stirred at room temperature for 45 mins. Ethyl acetate (20 ml) and then water (20 ml) were added to the reaction mixture. The layers were separated and the organic extract was dried over magnesium sulphate. Concentration in vacuo yielded a crude solid which was purified by flash chromatography over silica gel, eluting with a 1:1 (v/v) mixture of ethyl acetate/hexane to yield ($\pm$)-2-hydroxyethylidene-N-methyl-1-(quinolin-3-yl) cyclohexane carbothioamide (100 mg, 0.31 mmol) as a white solid, m.p. 104°–110° C.;

[N.M.R. (CDCl$_3$): 1.40–2.00 (c, 6H), 2.10–2.38 (m, 1H), 2.58–2.72 (dt, 1H), 3.12–3.26 (m, 1H), 3.28–3.32 (d, 3H), 4.22–4.30 (dd, 2H) 5.12–5.22 (dt, 1H), 7.46–7.58 (m, 1H), 7.64–7.78 (m, 2H), 7.88–7.92 (d, 1H), 8.00–8.06 (dd, 1H), 8.06–8.20 (br s, 1H), 8.78–8.82 (d, 1H).

Found: C, 68.2; H, 6.7; N, 8.2%; Calculated for $C_{19}H_{22}N_2OS \cdot \frac{1}{2}H_2O$: C, 68.1; H, 6.9; N, 8.4%. m/z=326].

EXAMPLE 6

Compound F

A solution of triethyl phosphonoacetate (1.23 g, 5.5 mmol) at room temperature in dry tetrahydrofuran (50 ml) was treated with a 60% oil dispersion of sodium hydride (250 mg, 7.2 mmol). After 15 mins at room temperature ($\pm$)-N-methyl-2-oxo-1-(quinolin-3-yl)-cyclohexane carbothioamide (1.5 g, 5. 1mmol) was added in one portion and the resulting solution stirred for 16 hours at room temperature. Ethyl acetate (150 ml) and then water (100 ml) were added to the reaction mixture. The layers were separated and the organic extract was dried over magnesium sulphate. Concentration in vacuo yielded a crude gum which was purified by flash chromatography over silica gel, eluting with a 1:4 (v/v) mixture of ethyl acetate/hexane to yield a 5:2 trans/cis mixture of ($\pm$)-2-ethoxycarbonylmethylene-N-methyl-1-(quinolin-3-yl)cyclohexane carbothioamide as a white solid (220 mg, 0.6 mmol), m.p. 177°–179° C.;

[N.M.R. (CDCl$_3$): 1.06–1.26 (2 t, 3H), 1.40–1.96 (c, 4H), 2.14–2.36/2.38–2.56 (2 m, 2H), 2.64–2.82/2.96–3.10 (2m, 1H), 3.38–3.52/3.60–3.74 (2m, 1H), 3.94–4.18 (2 q, 2H), 5.08–5.14/5.90–5.96 (2 s, 1H), 7.56–7.68 (m, 1H), 7.72–7.82 (m, 1H), 7.96–8.10 (m, 2H), 8.14–8.20/8.30–8.36 (2d, 1H), 8.78–8.82/8.86–8.90 (2d, 1H), 9.48–9.62 (br d, 1H).

Found: C, 68.8; H, 6.7; N, 7.1%; Calculated for $C_{21}H_{24}N_2O_2S$: C, 68.5; H, 6.5; N, 7.6%].

EXAMPLE 7

Compound G

The cis/trans mixture prepared as in Example 6 was chromatographed over silica gel eluting with a 1:4 (v/v) mixture of ethyl acetate/hexane to yield pure ($\pm$)-trans-2-ethoxycarbonylmethylene-N-methyl-1-(quinolin-3-yl)cyclohexane carbothioamide as a white solid, m.p. 204°–206° C.;

[N.M.R. (CD$_3$SOCD$_3$) 1.06–1.18 (t, 3H), 1.40–1.84 (c, 4H), 2.38–2.60 (c, 2H), 2.96–3.12 (m, 1H), 3.12–3.16 (d, 3H), 3.60–3.74 (dt, 1H), 3.94–4.08 (q, 2H), 5.08–5.14

(s, 1H), 7.56-7.68 (m, 1H), 7.72-7.82 (m, 1H), 7.96-8.04 (dd, 2H), 8.14-8.20 (d, 1H), 8.78-8.82 (d, 1H), 9.48-9.62 (br d, 1H).

Found: C, 67.6; H, 6.6; N, 7.2; S, 8.4%; Calculated for $C_{21}H_{24}N_2O_2S$: C, 68.5; H, 6.6; N, 7.6; S, 8.7%].

EXAMPLE 8

Compound H

A solution of (±)-2 -(pyrid-3-yl)-2 -methyl-dithiocarbonyl-1-hydroxyethylidenecyclohexane (120 mg, 0.41 mmol) in tetrahydrofuran (5 ml) was treated with a solution of 33% methylamine in ethanol (5 ml). After 15 hrs at 25° C. the mixture was diluted with ethyl acetate (40 ml) and washed with water (50 ml). The organic phase was removed and dried over magnesium sulphate.

Concentration in vacuo afforded a crude oil which was purified by flash chromatography over silica gel, eluting with ethyl acetate/methanol (98:2 ) to yield (±)-2 -(2 -hydroxyethylidene)-N-methyl-1-(pyrid-3-yl)-cyclohexane carbothioamide (90 mg, 0.33 mmol) as a colourless gum. Solidification with diethyl ether/n-hexane afforded a white solid, m.p. 172°-173° C.; [N.M.R. ($CDCl_3/SOCD_3$): 1.28-1.54 (m, 1H), 1.56-1.88 (c, 4H), 1.98-2.26 (m, 1H), 2.58-2.72 (m, 1H), 3.00-3.18 (m, 1H), 3.18-3.24 (d, 3H), 3.94-4.08 (dd, 1H), 4.18-4.32 (dd, 1H), 5.00-5.10 (t, 1H), 6.30-6.90 (br s, 1H), 7.16-7.24 (m, 1H), 7.50-7.58 (m, 1H), 8.34-8.24 (m, 2H), 8.50-8.62 (br s, 1H).

Found: C, 65.1; H, 7.3; N, 9.9;%; Calculated for C C, 65.2; H, 7.3; N, 10.1%].

EXAMPLE 9

Compound I

A suspension of (±)-trans-2-ethoxycarbonylmethylene-N-methyl-1-(quinolin-3-yl)cyclohexane carbothioamide (1.3 g, 3.53 mmol) in ethanol (30 ml) at 25° C. was treated with 2 M sodium hydroxide (30 ml). After 2 hrs at 25° C. the mixture was diluted with water (50 ml) and extracted with ethyl acetate (2×50 ml). The organic phases were removed and dried over magnesium sulphate. Concentration in vacuo gave a colourless gum. Trituration with diethyl ether/hexane gave (±)-2-carboxymethylene-N-methyl-1-(quinolin-3-yl)-cyclohexane carbothioamide (1 g, 2.94 mmol) as a white foam;

[N.M.R. ($CD_3 SOCD_3$ ) 1.40-1.82 (c, 5H), 2.28-2.42 (m, 1H), 2.92-3.12 (m, 1H), 3.08-3.14 (d, 3H), 3.52-3.66 (m, 1H), 5.10 (s, 1H), 7.56-7.64 (dt, 2H), 7.70-7.80 (dt, 2H), 7.98-8.02 (d, 2H), 8.16-8.18 (d, 1H), 8.78-8.00 (d, 1H), 11.98-12.14 (br s, 1H).

Found: C, 63.5; H, 5.6; N, 7.1%; Calculated for $C_{19}H_{20}N_2O_2S$: C, 67.0; H, 5.9; N, 8.2% m/z=340 (M+H peak)].

EXAMPLE 10

Compound J

A solution of 2-(pyrid-3-yl)-2-methyl-dithiocarbonyl-1-(2-phenoxyethylidene)cyclohexane (750 mg, 2 mmol) in tetrahydrofuran (10 ml) at 25° C. was treated with a solution of 33% methylamine in ethanol (10 ml). After 2 hrs at 25° C. the solution was concentrated in vacuo. Purification over silica gel, eluting with ethyl acetate/n-hexane afforded (±)-2-(2-phenoxyethylidene)-N-methyl-1-(pyrid-3-yl)-cyclohexane carbothioamide (300 mg, 0.85 mmol) as a white solid, m.p. 121°-122° C.;

[N.M.R. ($CDCl_3$): 1.38-1.58 (m, 1H), 1.60-2.00 (c, 5H), 2.06-2.24 (m, 1H), 2.66-2.80 (m, 1H), 3.10-3.18 (d, 3H), 4.50-4.58 (dd, 1H), 4.64-4.76 (dd, 1H), 6.18-6.26 (t, 1H), 6.78-6.86 (dd, 1H), 6.90-7.02 (t, 1H), 7.18-7.34 (m, 3H), 7.46-7.52 (m, 1H), 7.66-7.86 (br s, 1H), 8.44-8.48 (m, 2H).

Found: C, 71.2; H, 6.9; N, 7.9%; Calculated for C - C, 71.6; H, 6.9; N, 7.9%].

EXAMPLE 11

Compound K

A solution of 2-(pyrid-3-yl)-2-methyldithiocarbonyl-1-(2-(4 -hydroxyphenoxy)ethylidene)-cyclohexane (1.6 g, 4.16 mmol) in tetrahydrofuran (50 ml) was treated with a solution of 33% methylamine in ethanol (30 ml). After 60 hrs at 25° C. the mixture was diluted with ethyl acetate (200 ml) and extracted with water. The organic phase was removed and dried over magnesium sulphate. Concentration in vacuo afforded a crude oil which was purified by flash chromatography over silica gel, eluting with ethyl acetate/n-hexane/dichloromethane (3:2:5) to yield (±)-2-(2-(4-hydroxyphenoxy)ethylidene)-N-methyl-1-(pyrid-3-yl)cyclohexane carbothioamide (1.28 g, 3.48mmol) as a white solid, m.p. 82°-88° C.;

[N.M.R. ($CDCl_3$): 1.18-2.02 (c, 5H), 2.04-2.22 (m, 1H), 2.66-2.82 (m, 1H), 3.14-3.24 (m, 1H), 3.18-3.24 (d, 3H) 4.26-4.54 (dd, 1H), 4.58-4.72 (dd, 1H), 5.16-5.24 (t, 1H), 6.68-6.84 (m, 4H), 7.28-7.36 (m, 1H), 7.56-7.62 (m, 1H), 7.78-7.88 (br s, 1H), 8.46-8.54 (m, 2H)

Found: C, 68.0; H, 6.9; N, 6.8%; Calculated for $C_{21}H_{24}N_2O_2S$: C, 68.4; H, 6.6; N, 7.6%].

EXAMPLE 12

Compound L

A solution of 2-(pyrid-3-yl)-2-methyldithiocarbonyl-1-(2-(4-nitrophenoxy)ethylidene)-cyclohexane (180mg, 0.44mmol) in tetrahydrofuran (5 ml) was treated with a solution of 33% methylamine in ethanol (5 ml). After 5 hrs at 25° C. the mixture was diluted with ethyl acetate (50 ml). The organic phase was removed and dried over magnesium sulphate. Concentration in vacuo afforded a crude oil which was purified by flash chromatography over silica gel, eluting with ethyl acetate/n-hexane (4:6) to yield a colourless gum. Solidification using diethyl ether/n-hexane yielded (±)-2-(2-(4-nitrophenoxy)ethylidene)-N-methyl-1-(pyrid-3-yl)cyclohexane carbothioamide (110 mg, 0.28 mmol) as a white solid, m.p. 201°-202° C.;

[N.M.R. ($CDCl_3$): 1.42-2.0 (c, 4H), 2.00-2.30 (m, 2H), 2.56-2.70 (dt, 1H), 3.08-3.24 (m, 1H), 3.22-3.26 (d, 3H), 4.62-4.80 (m, 2H), 5.26-5.34 (t, 1H), 6.86-6.98 (m, 2H), 7.22-7.32 (m, 2H), 7.52-7.60 (m, 1H), 7.62-7.78 (br s, 1H), 8.14-8.24 (m, 2H), 8.46-8.56 (m, 2H).

Found: C, 63.5; H, 5.9; N, 10.4%; Calculated for $C_{21}H_{23}N_3O_3S$: C, 63.5; H, 5.8; N, 10.6%].

EXAMPLE 13

Compound M

A solution of 2-(pyrid-3-yl)-2-methyldithiocarbonyl-1-(2-phenylthioethylidene)cyclohexane (300 mg, 0.78 mmol) in tetrahydrofuran (10 ml) was treated with a solution of 33% methylamine in ethanol (10 ml). After 18 hrs at 25° C. the mixture was diluted with ethyl acetate (50 ml) and extracted with water (50 ml). The organic phase was removed and dried over magnesium sulphate. Concentration in vacuo afforded a crude oil which was purified by flash chromatography over silica gel, eluting with ethyl acetate/n-hexane (1:1) to yield (±)-2-(2-phenylthioethylidene)-N-methyl-1-(pyrid-3-yl)cyclohexane carbothioamide (100 mg, 0.27 mmol) as a cream paste;

[N.M.R. (CDCl$_3$): 1.20–1.44 (m, 1H), 1.50–1.90 (m, 4H), 1.98–2.12 (dt, 1H), 2.58–2.70 (m, 1H), 3.02–3.14 (m, 1H), 3.06–3.14 (d, 3H), 3.44–3.56 (dd, 1H), 3.66–3.78 (dd, 1H), 5.00–5.18 (t, 1H), 7.12–7.40 (m, 7H), 7.48–7.66 (br s, 1H), 8.36–8.38 (d, 1H), 8.42–8.48 (dd, 1H).

Found: C, 67.6; H, 6.6; N, 7.3%; Calculated for $C_{21}H_{24}N_2S_2$: C, 68.4; H, 6.6; N, 7.6%].

EXAMPLE 14

Compound N

A solution of n-butyllithium in hexane (1.6 M, 0.96 ml) and diisopropylamine (0.22 ml, 1.54 mmol) at −78° C. was treated with a solution of 4-fluorobenzyltriphenylphosphonium chloride (630 mg, 1.54 mmol) in tetrahydrofuran (15 ml). After allowing the solution to warm −40° C. over 40 mins (±)-2-formylmethylene-N-methyl- 1-(quinolin-3-yl)cyclohexane carbothioamide (0.5 g, 1.54 mmol) was added. After 3hrs at 25° C., dilution with ethyl acetate (50 ml) and washing with water (50 ml) gave two layers. The organic phase was removed and dried over magnesium sulphate. Concentration in vacuo yielded a crude solid. Purification by flash chromatography over silica gel, eluting with ethyl acetate/n-hexane afforded a 9:1 cis/trans mixture of (±)-2-((4-fluorostyryl)methylene)-N-methyl-1-(pyrid-3-yl)cyclohexane carbothioamide (190 mg, 0.46 mmol) as a white solid, m.p. 100°–102° C. The pure trans product was isolated by reverse phase H.P.L.C.

[N.M.R. (CD$_3$SOCD$_3$) 1.55–1.70 (c, 2H), 1.80–1.95 (m, 1H), 2.05–2.10 (m, 1H), 2.36–2.45 (m, 1H), 2.88–2.95 (dt, 1H), 3.25–3.28 (d, 3H), 3.24–3.35 (m, 1H), 5.98–6.02 (d, 1H), 5.90–6.65 (m, 2H), 6.58–6.65 (m, 2H), 6.90–6.95 (m, 2H), 7.52–7.58 (dt, 1H), 7.70–7.75 (m, 2H), 7.75–7.82 (br s, 1H), 7.87–7.89 (d, 1H), 8.04–8.14 (d, 1H), (8.87–8.89).

Found: C, 75.3; H, 6.2; N, 6.5%; Calculated for $C_{26}H_{25}FN_2S$: C, 75.0; H, 6.1; N, 6.7%].

EXAMPLE 15

Compound O

A solution of (±)-2-methyldithiocarbonyl-2-(pyrid-3-yl)-1-formylmethylenecyclohexane syn/anti-4-fluorobenzyloxime (200 mg) in dry tetrahydrofuran (5 ml) was stirred at room temperature and a 33% ethanolic solution of methylamine (1 ml) was added. The solution was stirred for 48 h, concentrated in vacuo and the residue purified by silica gel chromatography, eluting with ethyl acetate/n-hexane (1:4) to give (±)-2-formylmethylene-N-methyl-1-(pyrid-3-yl)-cyclohexane carbothioamide syn/anti-4-fluorobenzyloxime (130 mg) as a white solid, m.p. 69°–70° C.;

[N.M.R. (CDCl$_3$): 1.4–2.4 (m, 6H), 2.65–2.9 (m, 1H), 3.15–3.2 (m, 1H), 3.3 (dd, 3H), 5.0 (d, 2H), 5.65 and 6.2 (d, 1H), 7.0–7.2 (m, 2H), 7.2–7.4 (m, 3H), 7.6 (m, 1H), 7.65 (br s, 1H), 8.2 (d, 1H), 8.5 (br s, 2H)

Found: C, 65.0; H, 6.2; N, 10.0%; Calculated for $C_{22}H_{24}FN_3OS$: C, 66.5; H, 6.1; N, 10.57%].

EXAMPLE 16

Compound P

By proceeding as in Example 15, but using (±)-2-methyldithiocarbonyl-2-(pyrid-3-yl)-1-formyl-methylenecyclohexane syn/anti-2,3-dihydroxypropyloxime in place of the (±)-2-methylidithiocarbonyl-2 -(pyrid-3-yl)-1-formylmethylenecyclohexane syn/anti-4-fluorobenzyloxime there was obtained (±)-2-formylmethylene-N-methyl-1-(pyrid-3-yl)cyclohexane carbothioamide syn/anti-2,3-dihydroxypropyloxime (180 mg), m.p 55°–57° C.;

[N.M.R. (CDCl$_3$): 1.4–1.95 (m, 4H) 2.1–2.3 (dt, 2H), 2.7 (d, 1H), 3.2 (d, 1H), 3.3 (d, 3H), 3.6 (dd, 1H), 3.7 (dd, 1H), 4.0 (m, 1H), 4.1 (m, 2H), 5.7 (d, 1H), 7.3 (q, 1H), 7.6 (br s, 1H), 8.2 (d, 1H), 8.5 (q, 1H).

Found: C, 58.4; H, 6.9; N, 10.9; S, 8.4%; Calculated for $C_{18}H_{25}N_3O_3S.\frac{1}{2}H_2O$: C, 58.0; H, 7.0; N, 11.3; S, 8.6%].

EXAMPLE 17

Compound Q

A solution of triphenylphosphine (2.35 g, 9 mmol) in anhydrous tetrahydrofuran (30 ml) was treated dropwise with diethyl azodicarboxylate (1.4 ml, 9 mmol) over 5 min at 0° C. The solution was stirred at this temperature for 30 min and ten treated with a solution of 2-hydroxy-2,N-dimethyl-1-(pyrid-3-yl)cyclohexane carbothioamide (1.59 g, 6 mmol) in anhydrous tetrahydrofuran (15 ml). The mixture was warmed to room temperature and stirred for 16 h. The solution was then poured into aqueous hydrochloric acid (0.5 M, 60 ml) and extracted with ethyl acetate (3×45 ml). The aqueous phase was basified with 2 M aqueous sodium carbonate solution and extracted with dichloromethane (3×45 ml). The organic extract was dried over magnesium sulphate and evaporated to give a pale brown oil This was subjected to flash chromatography over silica gel, eluting with ethyl acetate/methanol (98:2) to give (±)-2-methylene-N-methyl-1-(pyrid-3-yl)cyclohexane carbothioamide (0.25 g) as a colourless solid, m.p. 106.5°–108.5° C.;

[N.M.R. (CDCl$_3$): 1.5–1.58 (m, 1H), 1.64–1.82 (m, 3H), 2.07–2.13 (m, 2H), 2.4–2.47 ((m, 1H), 3.1–3.16 (m, 1H), 3.26–3.29 (d, 3H), 4.47–4.49 (m, 1H), 5.26 (s, 1H), 7.22–7.26 (m, 1H), 7.55–7.59 (m, 1H), 7.9–8.03 (br s, 1H), 8.46–8.49 (m,1H), 8.51–8.53 (m, 1H).

Found: C, 67.7; H, 7.3; N, 11.3%; Calculated for $C_{14}H_{18}N_2S$: C, 68.3; H, 7.4; N, 11.3%].

EXAMPLE 18

Compound R

A suspension of lithium aluminium hydride (36 mg, 0.93 mmol) at room temperature in dry tetrahydrofuran (8 ml) was treated dropwise with a dry tetrahydrofuran solution (5 ml) of 2-cyanomethylene-N-methyl-1-(quinolin-3-yl)cyclohexane carbothioamide (300 mg, 0.93 mmol). The mixture was stirred at room temperature for 10mins and cooled in an ice bath. Water (2 ml) was added dropwise followed by ethyl acetate (20 ml). The mixture was washed with an aqueous solution of Rochelle salt (sodium potassium tartrate) (20 ml) and the separated organic extract dried over magnesium sulphate. Concentration in vacuo yielded a crude solid which was purified by flash chromatography over silica gel, eluting with a 1:1(v/v) mixture of ethyl acetate/- hexane to yield a white solid. Crystallisation from ether/hexane gave (±)-trans-2-cyanomethyl-N-methyl-1-(quinolin-3-yl)cyclohexane carbothioamide (120 mg,

[N.M.R (CDCl$_3$): 1.38–1.70 (c, 3H), 1.70–2.10 (c, 4H), 2.22–2.30 (d, 1H), 2.30–2.38 (d, 1H), 2.88–3.04 (m, 1H), 3.02–3.06 (d, 3H), 3.78–3.92 (m, 1H), 7.52–7.62 (m, 1H), 7.64–7.74 (m, 1H), 7.78–7.84 (dd, 1H), 8.00–8.04 (dd, 1H), 8.20–8.22 (d, 1H), 8.96–9.10 (br s, 1H), 9.02–9.04 (d, 1H).

Found: C, 70.2; H, 6.6; N 13.0%; Calculated for $C_{26}H_{25}FN_2S$: C, 70.6; H, 6.5; N, 13.0%. m/z=323].

EXAMPLE 19

Compound S

A suspension of lithium aluminium hydride (135 mg, 3.54 mmol) at room temperature in dry tetrahydrofuran (20 ml) was treated dropwise with a dry tetrahydrofuran solution (10 ml) of 2-cyanomethylene-N-methyl-1-(pyrid-3-yl)cyclohexane carbothioamide (960 mg, 3.54 mmol). The mixture was stirred at room temperature for 10mins Water (5 ml) was added dropwise followed by ethyl acetate (50 ml). The mixture was washed with an aqueous solution of Rochelle salt (50 ml) and the separated organic extract dried over magnesium sulphate. Concentration in vacuo yielded a yellow gum which was purified by flash chromatography over silica gel, eluting with ethyl acetate to yield a pale yellow gum (610 mg, 2.23 mmol). Trituration with ether/hexane yielded (±)-trans-2-cyanomethyl-N-methyl-1-(pyrid-3-yl)cyclohexane carbothioamide (610 mg, 2.23 mmol), as a white solid, m.p. 177°–178° C.;

[N.M.R. (CDCl$_3$): 1.38–2.6 (c, 10H), 3.08–3.14 (d, 3H), 3.64–3.80 (m, 1H), 7.28–7.36 (m, 1H), 7.48–7.68 (br s, 1H), 7.72–8.00 (m, 1H), 8.52–8.60 (m, 1H).

Found: C, 65.5; H, 6.9; N 15.1%; Calculated for $C_{15}H_{19}N_3S$: C, 65.9; H, 7.0; N, 15.4% m/z=274].

EXAMPLE 20

Compound T 2-(2-Hydroxyethyl)-1-((N-methylimino)(4-methoxybenzylthio)methyl)-1-pyrid-3-yl)cyclohexane (500 mg, 1.25 mmol) was added to 98% formic acid (10 ml) and stirred at 0°–5° C. for 0.5 hr and warmed to room temperature. The solution was concentrated in vacuo to give a yellow oil which was purified by flash chromatography over silica gel, eluting with a 5:95 mixture of methanol/ethyl acetate to give (±)-trans-2-hydroxyethyl-N-methyl-1-(pyrid-3-yl)cyclohexane carbothioamide (60 mg), m.p. 199°–200° C.;

[N.M.R. (CDCl$_3$): 1.4 (m, 1H), 1.5–1.7 (m, 6H), 2.0 (m, 1H), 2.2 (m, 1H), 2.6 (q, 1H), 3.05 (m, 1H), 3.1 (d, 1H), 3.5–3.7 (m, 2H), 7.3 (q, 1H), 7.4 (br s, 1H), 8.4 (d, 1H), 8.5 (dd, 1H), 8.7 (d, 1H).

Found: C, 64.5; H, 8.1; N 9.7%; S, 11.3%; Calculated for $C_{26}H_{25}FN_2S$: C, 64.7; H, 8.0; N, 10.0%; S, 11.5%].

EXAMPLE 21

Compound U

A solution of (±)-trans-2-cyanomethyl-N-methyl-1-(pyrid-3-yl)cyclohexane carbothioamide (3 g, 10.8 mmol) in dry tetrahydrofuran (30 ml) was added dropwise at room temperature under argon to a stirred suspension of lithium aluminium hydride (1.25 g, 33 mmol) in dry tetrahydrofuran (75 ml). After the addition, the mixture was stirred at reflux for 1 hr, cooled and treated with Rochelle salt solution (20 ml) and ethyl acetate (50 ml). The layers were separated and the aqueous was extracted with ethyl acetate (30 ml). The combined extracts were washed with water, dried (MgSO$_4$) and concentrated in vacuo to give a yellow oil which was triturated with ether to give (±)-trans-2-(2-aminoethyl)-N-methyl-1-(pyrid-3-yl)cyclohexane carbothioamide (2 g) as a yellow solid;

[N.M.R. (CDCl$_3$) 1.0–1.1 (m, 1H), 1.4–1.8 (m, 4H), 2.0 (m, 1H), 2.1 (m, 1H), 2.5 (m, 2H), 2.7 (m, 4H), 3.1 (d, 3H), 3.15–3.3 (m, 2H), 7.25 (q, 1H), 7.9 (dt, 1H), 8.4 (dd, 1H), 8.7 (d, 1H)].

EXAMPLE 22

Compound V

A solution of (±)-trans-2-cyanomethyl-N-methyl-1-(pyrid-3-yl)cyclohexane carbothioamide (1 g, 3.66 mmol) in diethyl ether (20 ml) and methanol (20 ml) was treated with gaseous hydrogen chloride until the solution was saturated. The mixture was then stirred for 3 hr and allowed to stand overnight. The mixture was then treated with water (10 ml) and adjusted to pH12 by addition of 5%(w/v) sodium hydroxide solution. The basified mixture was extracted with ethyl acetate (100 ml). The organic layer was separated and dried over magnesium sulphate. Filtration and concentration in vacuo yielded a colourless gum which was purified by flash chromatography over silica gel, eluting with ethyl acetate to yield (±)-trans-2-methoxycarbonyl-methyl-N-methyl-1-(pyrid-3-yl)cyelohexane carbothioamide (150 mg, 0.5 mmol), as a white solid, m.p.158°–159° C.;

[N.M.R. (CDCl$_3$): 1.40–1.60 (c, 3H), 1.68–1.76 (m, 2H), 1.88–2.0 (c, 2H), 2.08–2.16 (m, 1H), 2.28–2.35 (dd, 1H), 2.68–2.7 (m, 1H), 3.12–3.16 (d, 3H), 3.60 (s, 3H), 3.68–3.75 (m, 1H), 7.25–7.30 (dd, 1H), 7.78–7.86 (br, 1H), 7.94–7.98 (dt, 1H), 8.48–8.52 (dd, 1H), 8.58–8.62 (d, 1H).

Found: C, 62.5; H, 7.2; N 9.2%; Calculated for $C_{15}H_{19}N_3S$: C, 62.7; H, 7.2; N, 9.1% m/z=306].

EXAMPLE 23

Compound W

A solution of 2-formylmethyl-1-((N-methylimino)-(4-methoxybenzylthio)methyl)-1-(pyrid-3-yl)cyclohexane (700 mg, 1.77 mmol) in anhydrous toluene (40 ml) was treated with 0-benzylhydroxylamine hydrochloride (282 mg, 1.77 mmol) and the mixture was heated at reflux for 30 min and then allowed to cool to 25° C. Ethyl acetate (100 ml) was added to the reaction mixture. The organic solution was washed with water (100 ml) and then with saturated brine (100 ml). The layers were separated and the organic extract was dried over magnesium sulphate, filtered and the solvents removed in vacuo to yield a colourless gum. Trituration with hexane/diethyl ether gave (±)-trans-2-formylmethyl-N-methyl-1-(pyrid-3-yl)cyclohexane carbothioamide syn/anti-benzyloxime (240 mg, 0.63 mmol), as a white solid, m.p. 158°–160° C.;

[N.M.R. (CDCl$_3$): 1.35–1.88 (c, 4H), 2.05–2.20 (m, 2H), 2.48–2.50 (m, 2H), 3.05–3.12 d, 3H), 3.28–3.38 (m, 1H), 4.96–5.04 (d, 2H), 6.55–6.59/7.14–7.18 (2dd, 1H), 7.20–7.40 (c, 7H), 7.85–7.92 (m, 1H), 8.46–8.54 (m, 1H), 8.62–8.66 (m, 1H).

Found: C, 69.23; H, 7.18; N 10.95%; Calculated for $C_{26}H_{25}FN_2S$: C, 69.25; H, 7.13 N, 11.01% m/z=382 (m+H peak)].

EXAMPLE 24

Compound X

An ice-cold solution of anisole (0.2 ml) in triflucroacetic acid (2 ml) at 0° C. was treated with (±)-2-(2-benzoyloxyethyl)-1-[N-methylimino)(4-methoxybenzylthio)methyl]-1-(pyridyl-3-yl)cyclohexane (270 mg). After 10 minutes at 0° C. the solution was adjusted to pH12 by treatment with cold aqueous sodium hydroxide solution (25% w/v). The mixture was diluted with water (50 ml) and then extracted with ethyl acetate (50 ml). The organic extract was dried over magnesium sulphate and concentrated in vacuo, to give a crude oil which was subjected to flash chromatography on silica gel, eluting with a mixture of ethyl acetate and hexane (3:2 v/v) to give a white foam (150 mg). Trituration with hexane gave a white solid, which was recrystallised from a mixture of ethyl acetate and hexane, to give (±)-trans-2-benzoyloxyethyl-N-methyl-1-(pyrid-3-yl)cyclohexane carbothioamide (120 mg), m.p. 179°-180° C.;

[N.M.R. (CDCl$_3$): 1.35-I.84 (c, 7H), 2.04-2.26 (m, 2H), 2.54-2.7 (m, 1H), 3.08-3.14 d, 3H), 3.2-3.36 (m, 1H), 4.1-4.38 (m, 2H), 7.16-7.24 (dd, 1H), 7.38-7.62 (c, 4H), 7.9-8.06 (c, 3H), 7.46-7.52 (dd, 2H), 7.62-7.66 (d, 1H);

Found: C, 68.9; H, 6.8; N, 7.3%; Calculated for $C_{26}H_{25}FN_2S$: C, 69.07; H, 6.85; N, 7.33%; m/z=382].

EXAMPLE 25

Compound Y

By proceeding in a manner similar to that described hereinbefore in Example 24, but using as starting material the appropriate quantity of 2-(2-acetoxyethyl)-1-[N-methylimino)(4-methoxy-benzylthio)methyl]-1-(pyridyl-3-yl)cyclohexane, and triturating with a mixture of diethyl ether and hexane, there was prepared (±)-trans-2-acetoxyethyl-N-methyl-1-(pyrid-3-yl)cyclohexane carbothioamide in the form of a white solid, m.p. 139°-140° C.;

[N.M.R. (CDCl$_3$): 1.2-1.34 (m, 2H), 1.35-1.7 (c, 5H), 2.02 (s, 3H), 1.94-2.16 (m, 2H), 2.6-2.74 (m, 1H), 3.08-3.14 (d, 3H), 3.10-3.20 (m, 1H), 3.86-3.95 (m, 1H), 4.04-4.1 (m, 1H), 7.25-7.32 (dd, 1H), 7.68-7.78 (brs, 1H), 7.92-7.98 (dd, 1H), 8.48-8.52 (dd, 1H), 8.58-8.62 (d, 1H);

Found: C, 63.5; H, 7.5; N, 8.8%; Calculated for $C_{26}H_{25}FN_2S$: C, 63.71; H, 7.54; N, 8.74%; m/z=320].

REFERENCE EXAMPLE 1

A vigorously stirred solution of (±)-2-(pyrid-3-yl)cyclohexanone (5.5 g, 30 mmol) in anhydrous tetrahydrofuran 50 ml) under argon at −15° C. was treated with potassium t-butoxide (3.36 g, 30 mmol).

After 60 minutes at 0° C., a solution of methyl isothiocyanate (2.4 g, 33 mmol) in anhydrous tetrahydrofuran (10 ml) was added during 5 minutes. After 2.5 hours at 0° C. the solution was warmed to 20° C. and then poured into a saturated aqueous brine solution (250 ml). The mixture was extracted with ethyl acetate (50 ml) and then with chloroform (3×50 ml). The combined organic extracts were dried over sodium sulphate and the concentrated in vacuo (30° C.; 14 mmHg).

The crude product was recrystallised from methanol to give (±)-N-methyl-2-oxo-1-(pyrid-3-yl)-cyclohexane carbothioamide (4.8 g, 19 mmol), m.p. 188°-190° C.;

[N.M.R. (CDCl$_3$): 1.62-2.06 (m, 4H), 2.42-2.60 (m, 2H), 2.60-2.82 (m, 1H), 2.84-3.06 (m, 1H), 3.16-3.2 (d, 3H), 7.24-7.34 (ddd, 1H), 7.6-7.68 (ddd, 1H), 8.43-8.47 (d, 1H), 8.48-8.54 (dd, 1H), 8.9-9.2 (br s, 1H).

Found: C, 62.9; H, 6.6; N, 11.3; S, 13.1%; Calculated for $C_{13}H_{16}N_2OS$: C, 62.9; H, 6.5; N, 11.3; S, 12.9%].

REFERENCE EXAMPLE 2

A solution of (±)-trans-1-[(pyrid-3-yl)-bromomethyl]cyclopentanol (10.24 g, 40 mmol) in anhydrous tetrahydrofuran (500 ml) at 0° C. was treated, dropwise during 30 minutes, with a solution of silver perchlorate (9.9 g, 48 mmol) in anhydrous tetrahydrofuran (50 ml). After 60 minutes at 0° C. the mixture was poured into a mixture of saturated aqueous brine solution (500 ml) and 10% w/v aqueous sodium bicarbonate solution (500 ml). The resulting mixture was filtered and then extracted with ethyl acetate (2×500 ml). The combined organic extracts were washed with brine and then dried over sodium sulphate. Concentration in vacuo (30° C.; 14 mmHg) afforded a crude oil which was recrystallised from cyclohexane (120 ml) to give (±)-2-(pyrid-3-yl)-cyclohexane (6.7 g, 38 mmol), m.p. 78°-80° C.;

[N.M.R. (CDCl$_3$): 1.72-2.12 (m, 4H), 2.12-2.40 (m, 2H), 2.40-2.64 (m, 2H), 3.56-3.72 (dd, 1H), 7.22-7.32 (m, 1H), 7.44-7.54 (ddd, 1H), 8.34-8.42 (dd, 1H), 8.46-8.54 (dd, 1H)].

REFERENCE EXAMPLE 3

A solution of 3-cyclopentylidenemethylpyridine (62.2 g, 0.39 mol) in acetone (600 ml) and water (100 ml) was treated with a solution of concentrated sulphuric acid (18.9 g, 0.19mol) in water (100 ml) at 5° C. The ice-cold solution was treated with 1,3-dibromo-5,5-dimethylhydantoin (55 g, 0.19 mol) during 20 minutes After 3.5 hours at 0° C. the mixture was treated with sodium bicarbonate (33.6 g, 0.4 mol) followed by water (2 l) and then extracted with ethyl acetate (2×500 ml). The organic phase was removed and washed with 10% w/v aqueous sodium bicarbonate solution (500 ml) followed by water (200 ml) and brine (200 ml). The crude extract was dried over sodium sulphate and then filtered through a column of flash silica gel (10 cm×2.4 cm diameter). After concentration in vacuo (20° C.; 14 mmHg) the dark oil crystallised on standing to give (±)-trans-1-[(pyrid-3-yl)bromomethyl]cyclopentanol (56 g, 0.22 mcl) m.p. 92°-94° C.;

[N.M.R. (CDCl$_3$) 1.36-2.06 (c, 8H), 2.32-2.46(br s, 1H), 5.02 (s, 1H), 7.24-7.34 (ddd, 1H), 8.0-8.1 (ddd, 1H), 8.52-8.56 (dd, 1H), 8.62-8.66 (d, 1H).

Found: C, 51.9; H, 5.6; Br, 30.6; N, 5.5%; Calculated for $C_{11}H_{14}BrNo$: C, 51.6; H, 5.5; Br, 31.2; N, 5.5%].

REFERENCE EXAMPLE 4

A suspension of cyclopentyltriphenylphosphonium bromide (226 g, 0.55 mol) in anhydrous tetrahydrofuran (1000 ml) at 2° C. was treated with vigorous stirring under an atmosphere of argon, with potassium t-butoxide (61.7 g, 0.55 mol). The dark red mixture was stirred at 5° C. for 80 minutes and then treated with pyridine-3-carbaldehyde (58.9 g, 0.55 mol) during a period of 20 minutes. The reaction mixture was stirred at 0° C. for 2 hours and then at 20° C. for 18 hours. The tetrahydrofuran was removed in vacuo (30° C.; 14 mmHg) and the residue extracted with pentane (2×500 ml). After treatment with decolourising charcoal (5 g), the mixture was filtered through a plug of flash silica gel (Merck 70-230 mesh; 13 cm×2 cm diameter). The filtrate was concentrated in vacuo (30° C., 14 mmHg; then 20° C., 0.01 mmHg) to afford 3-cyclopentylidenemethylpyridine (54 g, 0.34 mol) as an orange oil which was used without further purification;

[N.M.R. (CDCl₃): 1.6–1.95 (m, 4H), 2.4–2.65 (m, 4H), 6.26–6.34 (m, 1H), 7.16–7.25 (ddd, 1H), 7.56–7.65 (ddd, 1H), 8.52–8.52 (d, 1H)].

REFERENCE EXAMPLE 5

A 4:1 mixture of (±)-cis/trans-2-methoxy-1-(pyrid-3-yl)cyclohexanol (2 g, 10 mmol), toluene and phosphorus pentoxide (3.4 g, 24 mmol) was heated at reflux for 5 hours. The mixture was then filtered and the precipitate partitioned between 2 M sodium hydroxide solution (80 ml) and diethyl ether (25 ml). The aqueous layer was extracted with ether (3×25 ml) and the combined organic extracts were dried over sodium sulphate. Concentration in vacuo afforded a crude oil which was purified by flash chromatography to give 2-(pyrid-3-yl)cyclohexanone (0.7 g, 4 mmol).

REFERENCE EXAMPLE 6

To a solution of 2.5 M n-butyllithium in hexane (13.2 ml, 33 mmol) at −78° C. was added diethyl ether (15 ml) followed by a solution of 3-bromopyridine (4.7 g, 30 mmol) in ether (90 ml) over a period of 10 minutes. After 1 hour at −78° C. a solution of (±)-2-methoxycyclohexane (3.84 g, 30 mmol) in ether (20 ml) was added dropwise during 10 minutes. After 2 hours at −78° C. and 30 minutes at 0° C. the reaction mixture was warmed to 20° C. and then poured onto ice (150 g). The mixture was extracted with ether (2×50 ml) and then the combined organic extracts were extracted with 1 N hydrochloric acid (50 ml). This aqueous extract was washed with ether (20 ml) and then treated with 2 M sodium hydroxide solution (25 ml) and extracted with ether (3×100 ml). The organic extracts were combined, washed with brine then dried over anhydrous sodium sulphate. Concentration in vacuo afforded (±)-2-methoxy-1-(pyrid-3-yl)cyclohexanol (5.0 g, 24 mmol) as a 4:1 mixture of cis and trans isomers;

[N.M.R. (CDCl₃): 1.2–2.14 (c), 2.24–2.44 (m), 2.90–3.28 (c), 3.48–3.60 (m), 7.18–7.30 (m), 7.78–7.96 (m), 8.40–8.48 (m), 8.62–8.72 (m), 8.78–8.82 (m)].

REFERENCE EXAMPLE 7

A solution of (±)-2-(quinolin-3-yl)-cyclohexanone (0.78 g, 3.5 mmol) in tetrahydrofuran (10 ml) at −5° C. was treated with potassium t-butoxide (0.43 g, 3.9 mmol). After 25 minutes at −5° C., the deep red mixture was treated dropwise during 1 minute with a solution of methyl isothiocyanate (0.28 g, 3.9 mmol) in tetrahydrofuran (2 ml). After 4 hours at 0° C. the reaction mixture was partitioned between saturated aqueous ammonium chloride solution (50 ml) and chloroform (50 ml). The aqueous layer was extracted again with chloroform (50 ml). The combined organic extracts were then dried over sodium sulphate and concentrated in vacuo (20° C.; 14 mmHg) to give a crude oil which was purified by flash chromatography over silica gel, eluting with ethyl acetate to give
(±)-N-methyl-2-oxo-(quinolin-3-yl)cyclohexane carbothioamide (0.1 g, 0.33 mmol), m.p. 235°–236° C.;

[N.M.R. (CDCl₃): 1.7–2.18 (c, 4H), 2.46–2.64 (m, 2H), 2.72–2.90 (m, 1H), 2.96–3.16 (m, 1H), 3.16–3.22 (d, 3H), 7.50–7.62 (ddd, 1H), 7.66–7.76 (ddd, 1H), 7.76–8.02 (dd, 1H), 8.04–8.12 (dd, 1H), 8.78–8.80 (d, 1H), 8.92–9.18 (br s, 1H).

Found: C, 68.0; H, 5.8; N, 9.0; S, 10.4%; Calculated for $C_{17}H_{18}N_2OS$: C, 68.4; H, 6.1; N, 9.4; S, 10.7%].

REFERENCE EXAMPLE 8

A solution of (±)-trans-1-[(quinolin-3-yl)-bromomethyl]cyclopentanol (1.1 g, 3.6 mmol) in tetrahydrofuran (20 ml) at 0° C. was treated, dropwise during 2 minutes, with a solution of silver perchlorate (0.893 g, 4.3 mmol) in tetrahydrofuran (5 ml). After 1 hour at 0° C. a mixture of saturated brine solution (20 ml) and saturated aqueous sodium bicarbonate solution (20 ml) was added to the reaction mixture. Ethyl acetate (40 ml) was then added and the resulting mixture was filtered through diatomaceous earth. The aqueous layer was removed and extracted with ethyl acetate (50 ml). The combined organic extracts were washed with brine (30 ml), dried over sodium sulphate, then concentrated in vacuo to afford (±)-2-(quinolin-3-yl)cyclohexanone (0.8 g, 3.5 mmol) as an oil which solidified on standing, m.p. 114°–115° C.;

[N.M.R. (CDCl₃) 1.72–2.68 (c, 8H), 3.74–3.88 (dd, 1H), 7.46–7.56 (ddd, 1H), 7.62–7.70 (ddd, 1H), 7.72–7.82 (d, 1H), 7.88–7.96 (d, 1H), 8.04–8.12 (d, 1H), 8.68 (d, 1H)].

REFERENCE EXAMPLE 9

A mixture of 3-cyclopentylidenemethylquinoline (3 g, 14 mmol), water (100 ml), dimethyl sulphoxide (50 ml), acetone (100 ml) and concentrated sulphuric acid (3.4 ml, 35 mmol) at 5° C. was treated with 1,3-dibromo-5,5-dimethylhydantoin (4.0 g, 14 mmol). After 5 minutes at 5° C. the mixture was stirred for 2 hours at 20° C. The mixture was filtered and washed with ethyl acetate (2×50 ml). The aqueous phase was then treated with saturated aqueous sodium bicarbonate solution (50 ml) and extracted with ethyl acetate (100 ml). The organic phase was then washed with water (50 ml) and brine (50 ml) then dried over sodium sulphate. Concentration in vacuo afforded a crude oil which was purified by flash chromatography, eluting with a 1:1 (v/v) mixture of diethyl ether and hexane and then ether. The product so obtained was then recrystallised from cyclohexane to give (±)-trans-1-[(quinolin-3-yl)-bromomethyl]cyclopentanol (1.1 g, 3.6 mmol);

[N.M.R.: 1.4–1.85 (c, 4H), 1.8–2.06 (c, 4H), 5.06 (s, 1H), 7.44–7.56 (ddd, 1H), 7.60–7.72 (ddd, 1H), 7.74–8.02 (dd, 1H), 8.04–8.12 (dd, 1H), 8.38–8.40 (dd, 1H), 9.0 (d, 1H)].

REFERENCE EXAMPLE 10

A solution of 2-chloro-3-cyclopentylidenemethylquinoline (7.6 g, 31.3 mmol) in glacial acetic acid (80 ml) at 60° C. was treated with zinc powder (4.0 g, 62.6 mmol). After stirring at 60° C. for 3 hours, the reaction mixture was cooled and then treated dropwise with 2 M sodium hydroxide solution (330 ml); the temperature being kept below 20° C. throughout. The resulting mixture was then extracted with ethyl acetate (2×250 ml). The combined organic extracts were dried over sodium sulphate then concentrated in vacuo to give a crude red oil (8 g) which was extracted with hot pentane (2×200 ml). Concentration of the combined extracts in vacuo (20° C.; 14 nmmHg) afforded 3-cyclopentylidenemethylquinoline (4 g, 31 mmol) which was used without further purification;

[N.M.R. (CDCl₃): 1.6–1.96 (m, 4H), 2.5–2.72 (m, 4H), 6.50 (m, 1H), 7.46–7.58 (ddd, 1H), 7.60–7.68 (ddd, 1H), 7.76–7.80 (dd, 1H), 8.0–8.08 (c, 2H)].

REFERENCE EXAMPLE 11

A suspension of cyclopentyltriphenylphosphonium bromide (4.1 g, 10 mmol) in tetrahydrofuran (50 ml) at 0° C. was treated with potassium t-butoxide (1.1 g, 10 mmol) portionwise during 5 minutes. After 1 hour at 0° C. the deep red mixture was treated with 2-chloroquinoline-3-carbaldehyde (1.9 g, 10 mmol).

After 4 hours at 0° C., hexane (250 ml) followed by brine (50 ml) was added to the reaction mixture. The organic layer was removed and dried over sodium sulphate. After concentration in vacuo (30° C., 14 mmHg) the crude oil was recrystallised from hexane to give 2-chloro-3-cyclopentylidenemethylquinoline (1.7 g, 7 mmol), m.p. 84°–86° C.;

N.M.R. (CDCl$_3$): 1.64–1.90 (m, 4H), 2.44–2.66 (m, 4H), 6.52 (m, 1H), 7.44–7.56 (ddd, 1H), 7.58–7.68 (ddd, 1H), 7.70–7.78 (dd, 1H), 7.92–8.00 (dd, 1H), 8.04 (s, 1H)

Found: C, 74.3; H, 5.8; Cl, 14.6; N, 5.7%; Calculated for C$_{15}$H$_{14}$ClN: C, 73.9; H, 5.7; Cl, 14.6; N, 5.7%].

REFERENCE EXAMPLE 12

A mixture of 3:1-cis:trans-($\pm$)-2-methoxy-1-(quinolin-3-yl)cyclohexanol (1.35 g, 5.3 mmol) and 40% (w/v) sulphuric acid (25 ml) was refluxed for 1 hour. The cooled mixture was basified with 1 M sodium carbonate solution (200 ml) and the mixture extracted with ethyl acetate (3×125 ml). The combined organic extracts were washed with brine (30 ml) then dried over sodium sulphate. Concentration in vacuo afforded a crude oil (1.4 g) which was recrystallised from a 4:1 (v/v) mixture of hexane and ethyl acetate (20 ml) to give ($\pm$)-2-(quinolin-3-yl)-cyclohexanone (0.53 g, 2.3 mmol), m.p. 114°–115° C.

REFERENCE EXAMPLE 13

A 2.5 M solution of n-butyllithium in hexane (18 ml) in ether (30 ml) at −78° C. was treated dropwise with a solution of 3-bromoquinoline (4.7 g, 22.5 mmol) in ether (30 ml). After 1 hour at −78° C. a solution of ($\pm$)-2-methoxycyclohexanone (5.8 g, 45 mmol) in ether (30 ml) was added dropwise during 35 minutes to the reaction mixture, which was maintained at −78° C. for 2 hours then at 0° C. for 1 hour and then warmed to 20° C. during 1 hour. The reaction mixture was poured onto ice (50 g) and water (50 ml) and the resulting aqueous layer extracted with ether (3×50 ml). The combined organic extracts were treated with 2 M hydrochloric acid (75 ml) and the organic phase discarded The aqueous layer was washed with ether (2×30 ml) and then basified with 2 M sodium hydroxide solution (75 ml). The aqueous layer was then extracted with ether (4×50 ml). The combined organic extracts were washed with brine (30 ml), dried over sodium sulphate and then concentrated in vacuo to afford a crude oil which was recrystallised from a 4:1 (v/v) mixture of hexane and ethyl acetate (60 ml) to give a 3:1 mixture of ($\pm$)-cis-and trans-2-methoxy-1-(quinolin-3-yl)-cyclohexanol (3.2 g, 12 mmol), m.p. 114°–115° C.;

[N.M.R. (CDCl$_3$): essential features 3.06 (s, trans OMe), 3.12 (s, cis OMe)].

REFERENCE EXAMPLE 14

A solution of 2-(pyrid-3-yl)-2-methyldithiocarbonyl-1-formylmethylenecyclohexane (890 mg, 3 mmol) in methanol (20 ml) at 25° C. was treated with sodium borohydride (127 mg, 3.36 mmol). After 30 mins at 25° C. the solution was treated with ethyl acetate (50 ml) and water (20 ml) was added dropwise. The organic phase was removed and dried over magnesium sulphate. Concentration in vacuo yielded a crude oil. Purification over silica gel, eluting with ethyl acetate/n-hexane (7:3) afforded 2-(pyrid-3-yl)-2-methyldithiocarbonyl-1-(2-hydroxyethylidene)cyclohexane (590 mg, 2 mmol) as an orange solid, m.p. 139°–140° C.;

[N.M.R. (CDCl$_3$): 1.46–1.80 (c, 5H), 1.84–1.98 (br s, 1H), 2.30–2.50 (c, 4H), 2.60 (s, 3H), 3.02–3.20 (m, 1H), 4.28–4.34 (d, 3H), 5.28–5.36 (t, 1H), 7.22–7.30 (m, 1H), 7.62–7.70 (m, 1H), 7.62–7.70 (m, 1H), 8.46–8.52 (dd, 1H), 8.58–8.62 (m, 1H).

Found: C, 61.0; H, 6.5; N 4.7%; Calculated for C$_{15}$H$_{19}$NOS$_2$: C, 61.4; H, 6.5; N, 4.8% m/z=293].

REFERENCE EXAMPLE 15

A solution of 2-(pyrid-3-yl)-2-methyldithiocarbonyl-1-cyanomethylenecyclohexane (7.2 g, 0.025 mol) in dichloromethane (200 ml) at 20° C. was treated with a solution of 1 M diisobutyl aluminium hydride in toluene (50 ml, 0.05 mol). The mixture was allowed to warm to 25° C. over 3 hours and diluted with dichloromethane (200 ml) and then washed with Rochelles solution (200 ml). The organic phase was removed, filtered through Celite, dried over magnesium sulphate and filtered. Concentration in-vacuo (50° C.; 20 mm Hg) afforded a crude gum which was purified by flash chromatography over silica gel, eluting with ethyl acetate/n-hexane (30:70) to give 2-(pyrid-3-yl)-2-ethyldithiocarbonyl-1-formylmethylenecyclohexane as an orange gum (3.17 g, 0.011 mol);

[N.M.R. (CDCl$_3$): 0.78–1.02 (c, 1H), 1.56–1.94 (c, 4H), 2.44–2.62 (m, 1H), 2.64 (s, 3H), 2.86–3.06 (m, 1H), 3.12–3.34 (m, 1H), 5.70–5.78 (d, 1H), 7.24–7.36 (m, 1H), 7.62–7.70 (m, 1H), 8.50–8.64 (m, 2H), 10.08–10.14 (d, 2H).

Found: C, 61.60, H, 6.09, N, 5.00%; Calculated for C$_{26}$H$_{25}$FN$_2$S: C; 61.82, H, 5.88, N, 4.81%].

REFERENCE EXAMPLE 16

A solution of diethyl cyanomethylphosphonate (18.2 g, 0.1 mol) in dry tetrahydrofuran (200 ml) at 25° C. was treated with sodium hydride (4.5 g of a 60% oil dispersion). After 30 mins at 25° C. the mixture was treated with 2-(pyrid-3-yl)-2-methyldithiocarbonylcyclohexanone (24.7 g, 0.93 mol) in dry tetrahydrofuran (100 ml). After 3 hrs at reflux the mixture was cooled to 25° C. over 30 mins, diluted with ethyl acetate (500 ml) and then washed with water (500 ml). The organic phase was removed and dried over magnesium sulphate and then filtered. Concentration in-vacuo (50° C.; 20 mm Hg) afforded a crude oil which wa purified by flash chromatography over silica gel, eluting with ethyl acetate/n-hexane (25:75) to give 2-(pyrid-3-yl)-2-methyldithiocarbonyl-1-cyanomethylenecyclohexane (7.4 g, 0.026 mol) as an orange gum.

REFERENCE EXAMPLE 17

A solution of 2-(pyrid-3-yl)cyclohexanone (20 g, 0.11 mol) in a dry tetrahydrofuran (200 ml) at −40° C. was treated with potassium tert-butoxide (16.7 g, 0.14 mol) After 15 mins at −40° C. the mixture was treated with carbon disulphide (10 ml, 0.165 mmol). The mixture was warmed to 25° C. over 30 mins. After 30 mins at 25° C. the mixture was treated with methyl iodide (10.3 ml, 0.165 mol). After 12 hrs at 25° C. the mixture was diluted with ethyl acetate (500 ml) followed by water (500 ml). The organic phase was removed, dried over magnesium sulphate and filtered. Concentration in-vacuo (50° C., 20 mm Hg) afforded a crude oil which was purified by flash chromatography over silica gel, eluting with ethyl acetate/n-hexane (30:70) to give 2-(pyrid-3-yl)-2-methyldithiocarbonylcyclohexanone (24.7 g, 0.09 mol) as an orange solid.

REFERENCE EXAMPLE 18

A solution of 2-methyldithiocarbonyl-2-(pyrid-3-yl)-1-formylmethylenecyclohexane (300 mg) was dissolved in toluene (10 ml) and heated at reflux with O-(4-fluorobenzyl)hydroxylamine hydrochloride (180 mg) for 3 hrs. After this time the mixture was cooled and concentrated in in-vacuo to give a brown oil. The oil was purified by silica gel chromatography using n-hexane/ethyl acetate (3:1) as eluent to give (±)-2-methyldithiocarbonyl-2-(pyrid-3-yl)-1-formylmethylenecyclohexane syn/anti-4-fluorobenzyloxime (200 mg);

[N.M.R. (CDCl$_3$) 1.4–2.0 (m, 4H), 2.2–2.6 (m, 3H), 2.6 (d, 3H), 3.1 (m, 1H), 5.0 (d, 2H), 5.8 and 6.4 (d, 1H), 7.0–7.2 (m, 2H), 7.2–7.4 (m, 3H), 7.6 (m, 1H), 7.65 (br s, 1H), 8.2 (d, 1H), 8.5 (br s, 2H)].

REFERENCE EXAMPLE 19

A solution of 2-methyldithiocarbonyl-2-(pyrid-3-yl)-1-formylmethylenecyclohexane (220 mg) was heated at reflux in dry toluene (5 ml) and dry pyridine (5 ml) with 2,3-dihydroxypropyloxyamine hydrochloride (112 mg) for 3 hrs. After this time the mixture was cooled and concentrated in-vacuo. The residue was treated with water and extracted with dichloromethane. Evaporation gave a brown oil which was purified by silica gel chromatography using ethyl acetate/methanol (95:5) as eluent to give (±)-2-methyldithiocarbonyl-2-(pyrid-3-yl)-1-formylmethylenecyclohexane syn/anti-2,3-dihydroxypropyloxime (50 mg);

N.M.R. (CDCl$_3$) 1.4–2.6 (m, 7H), 2.6 (d, 3H), 3.2 (d, 1H), 3.6 (dd, 1H), 3.7 (dd, 1H), 4.0 (m, 1H), 4.1 (m, 2H), 5.7 (d, 1H), 7.3 (q, 1H), 7.6 (br s, 1H) 8.2 (d, 1H), 8.5 (q, 1H)].

REFERENCE EXAMPLE 20

A solution of (±)-N-methyl-2-oxo-1-(pyrid-3-yl)cyclohexane carbothioamide (10 g, 0.04 mol) in dry tetrahydrofuran (100 ml) was stirred under an atmosphere of argon and treated portionwise with sodium hydride (1.8 g as a 60% dispersion in oil).

The solution was then added dropwise to a 3 M solution of methylmagnesium bromide in diethyl ether (47 ml, 0.14 mol) with stirring, under argon, maintaining the temperature below 10° C. The resulting mixture was stirred at room temperature for 2 h, cooled in an ice bath and treated with 15% (w/v) aqueous ammonium chloride solution (100 ml). The mixture was then extracted with ethyl acetate (3×100 ml) and the extract dried (MgSO$_4$) and concentrated in vacuo to give a crude gum. Flash chromatography over silica gel, eluting with cyclohexane/ethyl acetate/isopropanol (5:4:1) gave (±)-2-hydroxy-2,N-dimethyl-1-(pyrid-3 -yl)-cyclohexane carbothioamide (2.5 g) as a colourless gum.

[N.M.R. (CDCl$_3$): 1.38–1.8 (m, 5H), 2.14–2.66 (m, 3H), 3.05–3.11 (d, 3H), 3.45–3.62 (br s, 1H), 7.17–7.28 (m, 1H) 8.08–8.18 (m, 1H), 8.37–8.43 (m, 1H), 8.94–9.12 (br s, 1H), 9.22–9.3 (m, 1H)].

REFERENCE EXAMPLE 21

A mixture of 2-formylmethyl-1-((N-methylimino)-(4-methoxybenzylthio)methyl)-1-(pyrid-3-yl)cyclohexane (1 g, 2.52 mmol) and aluminium isopropoxide (1.03 g, 5.04 mmol) in dry isopropanol (50 ml) were heated at reflux under a McIntyre head under argon for 5 hr. After cooling, the solution was concentrated in vacuo and the residue treated with dichloromethane (50 ml) and Rochelle salt solution (20 ml). The layers were filtered and separated, and the organic layer washed with water, dried (MgSO$_4$) and concentrated in vacuo to give a cream solid. Recrystallisation from ethyl acetate gave 2-(2-hydroxyethyl)-1-((N-methylimino)-(4-methoxybenzylthio)methyl)-1-(pyrid-3-yl)cyclohexane (0.5 g) as a white solid, m.p. 145°–146° C.;

[N.M.R. (CDCl$_3$): 1.0 (m, 1H), 1.2–1.4 (m, 2H), 1.4–1.55 (m, 3H), 1.7–1.8 (br, 1H), 1.9 (dt, 1H), 2.0 (m, 1H), 2.7 (d, 1H), 2.85 (br d, 1H), 3.1 (d, 1H), 3.4 (m, 1H), 3.55 (m, 1H), 3.6 (s, 1H), 3.7 (d, 1H), 3.75 (s, 3H), 6.7 (m, 3H), 7.25 (m, 1H), 7.65 (dd, 1H), 8.5 (dd, 1H), 8.65 (d, 1H).

Found:-C, 69.0; H, 7.6; N, 6.9%; S, 8.1%; Calculated for $C_{23}H_{30}N_2O_2S$: C, 69.3; H, 7.6; N, 7.0%; S, 8.0%].

REFERENCE EXAMPLE 22

A solution of diisobutylaluminium hydride (10.2 ml of a 1 M solution in dichloromethane, 10.2 mmol) was added dropwise under argon to a stirred solution of 2-cyanomethyl-1-((N-methylimino)(4-methoxybenzylthio)-methyl)-1-(pyrid-3-yl)cyclohexane (2 g, 5.1 mmol) in dry dichloromethane (60 ml) at −20° C. After addition, the mixture was stirred for 1 hr at −20° C. and then allowed to warm slowly to room temperature over 3 hr. The mixture was then treated with Rochelle salt solution, filtered and the layers separated. The aqueous was extracted with dichloromethane (50 ml) and the combined extracts washed with water, dried (MgSO$_4$) and concentrated in vacuo to give a golden oil. The oil was purified by flash chromatography over silica gel, eluting with ethyl acetate, to give 2-formylmethyl-1-((N-methyl)(4-methoxybenzylthio)methyl)-1-(pyrid-3-yl)cyclohexane (1 g);

[N.M.R. (CDCl$_3$): 1.2 (dt, 1H), 1.4 (m, 2H), 1.5 (m, 1H), 1.7 (m, 2H), 1.75 (dt, 1H), 2.1 (m, 1H), 2.3 (m, 1H), 2.8 (br d, 1H), 3.15 (d, 1H), 3.6 (br s, 1H), 3.65 (s, 3H), 3.7 (d, 1H), 3.75 (s, 3H), 6.7 (q, 4H), 7.25 (q, 1H), 7.6 (dt, 1H), 8.5 (dd, 1H), 8.65 (d, 1H),
9.2 (s, 1H)].

REFERENCE EXAMPLE 23

To a stirred suspension of (±)-trans-2-cyanomethyl-N-methyl-1-(pyrid-3-yl)cyclohexane carbothioamide (1 g, 3.7 mmol) in dry tetrahydrofuran (20 ml) at room temperature was added portionwise potassium t-butoxide (405 mg, 3.7 mmol). After stirring for 20 min the resulting clear solution was cooled to −20° C. and treated with 4-methoxybenzyl chloride (0.5 ml, (3.7 mmol). The resulting solution was stirred for a further 10 min at −20° C. before being allowed to warm slowly to room temperature. The mixture was then stirred for 2 hr and then treated with water and concentrated in vacuo. The residue was treated with water (20 ml) and extracted with ethyl acetate (2×30 ml). The combined organic extracts were washed with water, dried (MgSO$_4$) and concentrated in vacuo to give a yellow oil. The oil was purified by flash chromatography over silica gel, eluting with ethyl acetate, to give (±)-trans-2- cyanomethyl-1-((N-methylimino)(S-methoxybenzylthio)methyl)-1-(pyrid-3-yl)-cyclohexane (1 g);

[N.M.R. (CDCl$_3$): 1.2 (tt, 1H), 1.4 (m, 1H), 1.6 (br d, 1H), 1.8 (m, 4H), 2.1–2.3 (m, 2H), 2.8 (d, 1H), 3.15 (d, 1H), 3.25 (d, 1H), 3.6 (s, 3H), 3.7 (d, 1H), 3.75 (s, 3H), 6.7 (m, 4H), 7.3 (q, 1H), 7.6 (dt, 1H), 8.55 (dd, 1H), 8.6 (d, 1H)].

REFERENCE EXAMPLE 24

A solution of 2-(2-hydroxyethyl)-1-[(N-methylimino)(4-methoxybenzylthio)methyl]-1-(pyrid-3-yl)-cyclohexane (400 mg) in dichloromethane (10 ml) at 0° C. was treated with 4-dimethylaminopyridine (147 mg). The stirred mixture was treated dropwise with acetyl chloride (0.085 ml) and then it was allowed to warm to 25° C., with stirring, during one hour. The mixture was stirred for a further one hour at 25° C. and then it was diluted with dichloromethane (50 ml). The reaction mixture was washed with saturated aqueous sodium bicarbonate solution (50 ml). The organic layer was separated, dried over magnesium sulphate and evaporated in vacuo, to give an oil. The oil was subjected to flash chromatography on silica gel, using a mixture of ethyl acetate and hexane (3:2v/v) as eluant, to give 2-(2-acetoxyethyl)-1-[(N-methylimino)-(4-methoxybenzylthio)methyl]-1-(pyridyl-3-yl)cyclohexane (60 mg) in the form of a colourless gum;

N.M.R. (CDCl$_3$): Diagnostic signals 1.98 (s, 3H), 3.64 (s, 3H), 3.75 (s, 3H)].

REFERENCE EXAMPLE 25

By proceeding in a manner similar to that described hitherto in Reference Example 24, but using benzoyl chloride instead of acetyl chloride, there was prepared 2-(2-benzoyloxyethyl)-1-[(N-methylimino)(4-methoxybenzylthio)methyl]-1-(pyrid-3-yl)cyclohexane;

[N.M.R. (CDCl$_3$): Diagnostic signals 3.64 (s, 3H), 3.75 (s, 3H), 7.4–7.46 (m, 2H), 7.52–7.58 (m, 1H), 7.95–7.99 (m, 1H)].

The present invention includes within its scope pharmaceutical compositions which comprise a compound of general formula (I) or a pharmaceutically acceptable salt thereof, in association with a pharmaceutically acceptable carrier or coating. In clinical practice the compounds of the present invention may be administered rectally, but are preferably administered parenterally, by inhalation if appropriate, or, more preferably, orally.

Solid compositions for oral administration include compressed tablets, pills, powders and granules. In such solid compositions, one or more of the active compounds is, or are, admixed with at least one inert diluent such as starch, sucrose or lactose.

The compositions may also comprise, as is normal practice, additional substances other than inert diluents, e.g. lubricating agents, such as magnesium stearate.

Liquid compositions for oral administration include pharmaceutically acceptable emulsions, inert diluents commonly used in the art such as water and liquid paraffin. Besides inert diluents such compositions may comprise adjuvants, such as wetting, and suspending agents, and sweetening, flavouring, perfuming and preserving agents. The compositions according to the invention also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive and injectable organic esters such as ethyl oleate. The compositions may also contain adjuvants such as stabilising, preserving, wetting, emulsifying and dispersing agents. They may be sterilised by, for example, filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Compositions for inhalation may be sterile aqueous solutions which are then nebulised or dry powders formulated in accordance with known methods.

Solid compositions for rectal administration include suppositories formulated in accordance with known methods and containing one or more of the compounds of formula (I) or a pharmaceutically acceptable salt thereof.

The percentage of active ingredient in the composition of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration, the duration of the treatment, and the condition of the patient. In the adult, the doses are generally from 0.001 to 50 mg/kg body weight per day by oral administration. By inhalation, either as a nebulised solution or as a formulated dry powder, the preferred daily dosage is from 0.001 to 5 mg/kg body weight.

The compounds may also be applied topically for inhibition of head hair loss associated with male pattern baldness, the preferred daily dosage being from 0.1 to 10 mg/kg body weight applied, for example, in 5 ml portions two or three times per day.

The following Example illustrates a pharmaceutical composition according to the present invention.

COMPOSITION EXAMPLE

No. 2 size gelatin capsules each containing:

| | |
|---|---|
| (±)-2-cyanomethylene-N-methyl-1-(quinolin-3-yl)-cyclohexane carbothioamide (active ingredient) | 20 mg |
| Lactose | 100 mg |
| Starch | 60 mg |
| Dextrin | 40 mg |
| Magnesium stearate | 1 mg | were prepared in accordance with the usual procedure.

Similar capsules were prepared by replacing the active ingredient by (±)-trans-2-cyanomethyl-N-methyl-1-(quinolin-3-yl)cyclohexane carbothioamide.

We claim:

1. A thioformamide derivative of the general formula:

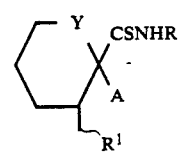

(I)

wherein:

R represents an alkyl group;

A represents:
pyrid-3-yl, quinolin-3-yl, or isquinolin-4-yl, $R^1$ represents:
hydrogen; an alkyl, cyano, carboxyl, formyl, carbamoyl, or alkoxycarbonyl group; or a group of the formula $-(CH_2)_nOR^2$, $-(CH_2)_nSR_2$, $-(CH_2)_nN(R^2)_2$, $-CH=CHR^3$, $-CH=NOR^4$, $-CONHR^5$, or $-COR^6$;

$R^2$, each of which may be the same or different when attached to nitrogen, represents:
hydrogen; an alkyl, alkanoyl, aryl, aryl(CH$_2$)$_n$— or arylCO— group; or, when attached to nitrogen, the two $R^2$ groups may together represent an alkylene group having three to six carbon atoms;

$R^3$ represents:
hydrogen; an alkyl, alkanoyl, carboxyl, carbamoyl, cyano, aryl, arylCO—, aryl(CH$_2$)$_n$—, or aryl(CH$_2$)$_n$CO— group; or an alkyl group substituted by a hydroxy, alkoxy or carboxyl group;

$R^4$ represents:
hydrogen; an alkyl, aryl, or aryl(CH$_2$)$_n$— group; or an alkyl group substituted by one or more groups selected from carboxyl, alkoxycarbonyl, hydroxy, alkoxy, carbamoyl, N-alkylcarbamoyl, N,N-dialkyl-carbamoyl, amino, alkylamino, and dialkylamino groups, alkenyl groups having two to four carbon atoms, amino and carbamoyl groups N,N-disubstituted by an alkylene group having three to six carbon atoms;

$R^5$ represents:
an alkyl, aryl, or aryl(CH$_2$)$_n$— group; or an amino acid residue wherein the nitrogen atom of the —CONHR$^5$ group is derived from an amine nitrogen atom of the amino acid;

$R^6$ represents:
an alkyl, aryl, or aryl(CH$_2$)$_n$— group; aryl indicates:
a carbocyclic, monocyclic or polycyclic, aromatic ring system which may be substituted by one or more substitutents selected from halogen atoms and hydroxy, alkyl, alkoxy, cyano, nitro, trifluoromethyl, carboxyl, alkoxycarbonyl, amino, alkylamino, dialkylamino, carbamoyl, N-alkylcarbamoyl, N,N-dialkylcarbamoyl and carboxyalkyl groups, and amino and carbamoyl groups N,N,-disubstituted by an alkylene group having three to six carbon atoms;

Y represents:
an ethylene or methylene group or a direct bond; the bond represented by is a single or double bond or, when $R^1$ represents a formyl group, represents a double bond; and n is an integer from 1 to 6;
wherein alkyl groups and moieties, including those in alkoxy, alkoxycarbonyl and alkanoyl groups, are straight-chain or branched and, unless otherwise specified, contain one to four carbon atoms, and stereoisomers and salts thereof.

2. A compound according to claim 1 wherein Y is a methylene group.

3. A compound according to claim 1 or 2 wherein n is one.

4. A compound according to claim 1, 2 or 3 wherein R is methyl.

5. A compound according to any one of the preceding claims wherein A is pyrid-3-yl or quinolin-3-yl.

6. A compound according to any one of the preceding claims which exhibits at least one of the following features:

(i) $R^1$ represents hydrogen or a cyano, carboxyl, formyl or alkoxycarbonyl group; or a group of the formula $-(CH_2)_nOR_2$, $-(CH_2)_nSR_2$, $-(CH_2)_nN(R^2)_2$, $-CH=CHR^3$, or $-CH=NOR^4$;

(ii) $R^2$ represents hydrogen or an alkanoyl, aryl or arylCO— group;

(iii) $R^3$ represents an aryl group;

(iv) $R^4$ represents an aryl or arylalkyl group; or an alkyl group substituted by one or more hydroxy groups; and (v) "aryl" indicates a phenyl group, which may be substituted by one or more substituents selected from halogen atoms and hydroxy and nitro groups.

7. A compound according, to any one of the preceding claims which exhibits at least one of the following features:

(i) $R^1$ represents hydrogen or a cyano, carboxyl, formyl, methoxycarbonyl, ethoxycarbonyl or hydroxymethyl group, or an optionally substituted phenoxymethyl group, a phenylthiomethyl group, an optionally substituted phenylvinyl group, an optionally substituted phenoxyiminomethyl group, a benzyloxyiminomethyl group, an optionally substituted alkoxyiminomethyl group, or an aminomethyl, benzoyloxymethyl or acetoxymethyl group;

(ii) $R^2$ represents hydrogen or an optionally substituted phenyl group or a benzoyl or acetyl group;

(iii) $R^3$ represents an optionally substituted phenyl group;

(iv) $R^4$ represents an optionally substituted phenyl group or an optionally substituted phenylmethyl group.

8. A compound according to claim 1 which is
($\pm$)-2-cyanomethylene-N-methyl-1-(pyrid-3-yl)cyclohexane carbothioamide,
($\pm$)-2-formylmethylene-N-methyl-1-(pyrid-3-yl)cyclohexane carbothioamide,
($\pm$)-2-cyanomethylene-N-methyl-1-(quinolin-3-yl)cyclohexane carbothioamide,
($\pm$)-2-formylmethylene-N-methyl-1-(quinolin-3-yl)cyclohexane carbothioamide,
($\pm$)-2-(2-hydroxyethylidene)-N-methyl-1-(quinolin-3-yl)-cyclohexane carbothioamide,
($\pm$)-trans/cis-2-ethoxycarbonylmethylene-N-methyl-1-(quinolin-3-yl)cyclohexane carbothioamide,
($\pm$)-trans-2-ethoxycarbonylmethylene-N-methyl-1-(quinolin-3-yl)cyclohexane carbothioamide,
($\pm$)-2-(2-hydroxyethylidene)-N-methyl-1-(pyrid-3-yl)-cyclohexane carbothioamide,
($\pm$)-2-carboxymethylene-N-methyl-1-(quinolin-3-yl)-cyclohexane carbothioamide,
($\pm$)-2-(2-phenoxyethylidene)-N-methyl-1-(pyrid-3-yl)-cyclohexane carbothioamide,
($\pm$)-2-(2-(4-hydroxyphenoxy)ethylidene)-N-methyl-1-(pyrid-3-yl)cyclohexane carbothioamide,
($\pm$)-2-(2-(4-nitrophenoxy)ethylidene)-N-methyl-1-(pyrid-3-yl)cyclohexane carbothioamide,
($\pm$)-2-((4-fluorostyryl)methylene)-N-methyl-1-(pyrid-3-yl)-cyclohexane carbothioamide,
($\pm$)-2-formylmethylene-N-methyl-1-(pyrid-3-yl)cyclohexane carbothioamide syn/anti-4-fluoro-benzyloxime, (±)-2-formylmethylene-N-methyl-1-(pyrid-3-yl)cyclohexane carbothioamide syn/anti-2,3-dihydroxypropyloxime,
(±)-2-methylene-N-methyl-1-(pyrid-3-yl)cyclohexane carbothioamide,
(±)-trans-2-cyanomethyl-N-methyl-1-(quinolin-3-yl)-cyclohexane carbothioamide,
(±)-trans-2-cyanomethyl-N-methyl-1-(pyrid-3-yl)cyclohexane carbothioamide,
(±)-trans-2-(2-aminoethyl)-N-methyl-1-(pyrid-3-yl)-cyclohexane carbothioamide,
(±)-trans-2-methoxycarbonylmethyl-N-methyl-1-(pyrid-3-yl)cyclohexane carbothioamide,
(±)-trans-2-formylmethyl-N-methyl-1-(pyrid-3-yl)cyclohexane carbothioamide syn/anti- benzyloxime,
(±)-trans-2-benzoyloxyethyl-N-methyl-1-(pyrid-3-yl)-cyclohexane carbothioamide or
(±)-trans-2-acetoxyethyl-N-methyl-1-(pyrid-3-yl)cyclohexane carbothioamide, or a pharmaceutically acceptable salt thereof.

9. A pharmaceutical composition which comprises as active ingredient a thioformamide derivative of general formula (I) as defined in claim 1, or a pharmaceutically acceptable salt thereof, in association with a pharmaceutically acceptable diluent or carrier.

* * * * *